United States Patent [19]

Lange et al.

[11] Patent Number: 5,238,908

[45] Date of Patent: Aug. 24, 1993

[54] HERBICIDAL GLUTARAMIC ACIDS AND DERIVATIVES

[75] Inventors: Barry C. Lange; John W. Ashmore; Jane Wissinger-Cornille, all of Lansdale, Pa.

[73] Assignee: Rohm and Haas Company, Philadelphia, Pa.

[21] Appl. No.: 563,779

[22] Filed: Aug. 9, 1990

Related U.S. Application Data

[63] Continuation-in-part of Ser. No. 401,268, Aug. 31, 1989, abandoned.

[51] Int. Cl.$^5$ .................. A01N 43/40; C07D 213/61; C07D 213/62; C07D 213/65
[52] U.S. Cl. ...................... 504/244; 504/254; 504/255; 504/256; 504/257; 504/259; 504/260; 546/286; 546/288; 546/289; 546/291; 546/292; 546/296; 546/298; 546/299; 546/300; 546/301; 546/302; 546/303; 546/304; 546/305; 546/306; 546/307; 546/308; 546/309; 546/310; 546/312
[58] Field of Search ............... 546/286, 288, 289, 291, 546/292, 308, 309, 310, 312; 560/129; 562/459, 464; 71/94, 79; 564/161, 162; 504/244, 254, 255, 256, 257, 259, 260

[56] References Cited

U.S. PATENT DOCUMENTS

| | | | |
|---|---|---|---|
| 4,489,010 | 12/1984 | Teach et al. | 562/433 |
| 4,509,975 | 4/1985 | Teach et al. | 71/100 |
| 4,557,756 | 12/1985 | Teach et al. | 71/118 |

FOREIGN PATENT DOCUMENTS

| | | |
|---|---|---|
| 391847 | 10/1990 | European Pat. Off. |
| 0001237 | 4/1989 | Switzerland . |
| 3869 | 10/1989 | Switzerland . |

Primary Examiner—Mukund J. Shah
Assistant Examiner—Y. N. Gupta
Attorney, Agent, or Firm—Terry B. Morris

[57] ABSTRACT

This invention relates to glutaramic acids and derivatives exhibiting herbicidal activity having the structure

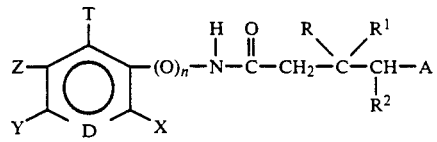

wherein A is a carboxylic acid or a derivative thereof, D is CH or N, and R, $R^1$, $R^2$, T, X, Y, and Z are as defined within, compositions containing these compounds and methods of controlling weeds with these compounds.

38 Claims, No Drawings

HERBICIDAL GLUTARAMIC ACIDS AND DERIVATIVES

This application is a continuation-in-part of application Ser. No. 401,268, filed Aug. 31, 1989, abandoned.

This invention relates to substituted glutaramic acids and derivatives which show activity as herbicides, to herbicidal compositions which contain these compounds and to methods of controlling weeds with these herbicidal compositions.

BACKGROUND OF THE INVENTION

During the past years, there has been an intensified search for herbicides to control unwanted plants U.S. Pat. Nos. 3,642,891, 3,723,474, 3,941,581, 4,489,010, 4,595,408, and 4,557,756 disclose N-(m-amidophenyl)-glutaramic acids and derivatives and their use as herbicides. No other substitution on the phenyl ring is disclosed.

There remains a need for additional herbicidal agents which are as effective or more effective than presently existing compounds.

SUMMARY OF THE INVENTION

The present invention is a new class of substituted glutaramic acids and glutaramic acid derivatives of the formula $$\text{Structure I}$$

wherein

A is hydroxymethyl ($CH_2OH$); chloromethyl ($CH_2Cl$); carboxy (COOH); carboxy salt (COO—M+); alkoxycarbonyl or alkylaminocarbonyl;

D is CH or N;

n is 0 or 1;

R is hydrogen (H), ($C_1$-$C_4$)alkyl, halo($C_1$-$C_4$)alkyl containing from one to nine halo atoms, or phenyl;

$R^1$ is hydrogen, ($C_1$-$C_2$)alkyl or halo($C_1$-$C_2$)alkyl;

$R^2$ is hydrogen or ($C_1$-$C_2$)alkyl;

T is hydrogen or fluorine (F);

X is hydrogen or halogen;

provided that when X and Z are each independently hydrogen or halogen, Y is halogen and D is CH, R must be trifluoromethyl ($CF_3$);

Y is hydrogen, halo($C_1$-$C_3$)alkyl, ($C_1$-$C_3$)alkyl, cyano, nitro ($NO_2$), halogen, phenoxy or phenylthio; provided when Y is hydrogen, R is trifluoromethyl ($CF_3$), $R^1$ and $R^2$ are hydrogen and Z is not hydrogen; and when Y is chlorine (Cl) and Z is a substituent linked to the phenyl ring by oxygen, R is not hydrogen;

Z is hydrogen; hydroxy (OH); halogen; alkoxyl; alkenyloxy; alkynyloxy; alkylthio; alkenylthio; alkynylthio; carboxyalkoxy; carboxyalkylthio; alkoxycarbonylalkoxy; alkoxycarbonylalkylthio; cycloalkoxy; cycloalkylalkoxy; cycloalkylthio; cycloalkylalkylthio; heterocyclylalkoxy; formyl; alkanoyl; alkoxycarbonyl; alkenyloxycarbonyl; alkynyloxycarbonyl; cycloalkoxycarbonyl; cycloalkylalkoxycarbonyl; alkoxycarbonylalkoxycarbonyl; alkyl; hydroxyalkyl; alkoxyalkyl; alkenyloxyalkyl; alkynyloxyalkyl; alkylthioalkyl; alkenylthioalkyl, alkynylthioalkyl; cycloalkoxyalkyl; cycloalkylalkoxyalkyl; cycloalkylthioalkyl; cycloalkylalkylthioalkyl; alkoxycarbonylalkoxyalkyl; phenoxyalkyl; phenylthioalkyl; alkylaminoalkyl; heterocyclyl; oximyl (—CH=NOH); alkyloximyl (—CH=NOalkyl); alkenyloximyl (—CH=NOalkenyl); alkynyloximyl (—CH=NOalkynyl); alkoxycarbonylalkyloximyl (—CH=NO(alkoxycarbonyl)alkyl); alkyl(alkyl)oximyl (—C(alkyl)=NOalkyl); alkenyl(alkyl)oximyl (—C(alkyl)=NOalkenyl); alkynyl(alkyl)oximyl (—C(alkyl)=NOalkynyl); alkoxycarbonylalkyl(alkyl)oximyl (—C(alkyl)=NO(alkoxycarbonyl)alkyl; alkylamino; monoalkenylamino; monoalkynylamino; alkylsulfonylamino; or alkanoylamino, provided when Z is acetamido, Y is not chloro; or Y and Z together form a heterocyclic ring fused to the phenyl ring to form a compound of the structure $$\text{Structures}$$

wherein

L is oxygen (O) or sulfur (S);

$R^3$ is hydrogen or alkyl;

$R^4$ is hydrogen; alkyl; alkenyl; alkynyl; alkoxyalkyl; alkenyloxyalkyl; alkynyloxyalkyl; alkoxycarbonylalkyl; cycloalkyl; cycloalkylalkyl; phenylalkyl; alkylthioalkyl; alkenylthioalkyl; alkynylthioalkyl; heterocyclylalkyl; alkylaminoalkyl; alkoxycarbonyl; or alkanoyl and M+ are agronomically acceptable salts thereof.

Alkyl means straight and branched alkyl groups, for example ($C_1$-$C_6$)alkyl such as methyl, ethyl, n-propyl, isopropyl, n-butyl, isobutyl, s-butyl or 1-ethylpropyl. An alkyl portion of any one of the substituents listed above for Z is optionally substituted by one to five halogens to form groups such as trifluoromethyl, 1,1,1,2,2-pentafluoroethyl, (trifluoromethyl)methyl; optionally substituted by phenyl to form such groups as benzyl or phenethyl. An alkyl portion of any one of the substituents listed above for Z or $R^4$ is optionally substituted by cyano to form groups such as cyanomethyl, 2-cyanoethyl or 1-cyanoethyl. Cycloalkyl is, for example, cyclopropyl, cyclobutyl, cyclopentyl, cyclohexyl and includes cycloalkyl optionally substituted by ($C_1$-$C_4$)alkyl, for example 2-methylcyclopropyl, or halo, for example 2,2-dichlorocyclopropyl. Phenyl is optionally substituted with one or two substituents such as ($C_1$-$C_3$)alkyl, halogen, ($C_1$-$C_3$)alkoxy or trifluoromethyl. Haloalkyl for R is, for example, fluoromethyl, difluoromethyl, trifluoromethyl, or pentafluoroethyl. Heterocyclyl is, for example, an optionally substituted aromatic or non-aromatic five-or six-membered ring containing from one to three atoms independently selected from nitrogen, oxygen or sulfur, such as pyridyl, tetrahydrofuranyl, or 5,5-dimethyloxazolinyl.

Halogen means fluorine, chlorine, bromine and iodine.

When listed for Y and Z, thio includes thio (—S—), sulfinyl (—SO—) and sulfonyl (—SO$_2$—).

Substituted amino groups such as alkylamino include mono-and di-substituted groups, for example, monoalkylamino and dialkylamino.

Oximes are in either the syn or anti configuration or are mixtures thereof.

Agronomically acceptable salts include those known in the art, for example, metal salts such as sodium, potassium, calcium and magnesium, ammonium salts such as ammonium and isopropylammonium and trialkylsulfonium salts such as trimethylsulfonium. Also included are Ethomeen salts.

Alkoxy is, for example (C$_1$-C$_6$)alkoxy such as methoxy, ethoxy, n-propyloxy, isopropyloxy, n-butyloxy, isobutyloxy, or s-butyloxy. Alkenyloxy is, for example, (C$_3$-C$_6$)alkenyloxy such as allyloxy. Alkynyloxy is, for example, (C$_3$-C$_6$)alkynyloxy such as propargyloxy, 1-methylpropargyloxy or 2-butynyloxy. Alkylthio is, for example, (C$_1$-C$_6$)alkylthio. Alkenylthio is, for example, (C$_3$-C$_6$)alkenylthio. Alkynylthio is, for example, (C$_3$-C$_6$)alkynylthio such as propargylthio. Cycloalkoxy is, for example, (C$_3$-C$_6$)cycloalkoxy. Cycloalkylalkoxy is, for example, (C$_3$-C$_6$)cycloalkyl(C$_1$-C$_6$)alkoxy. Cycloalkylthio is, for example, (C$_3$-C$_6$)cycloalkylthio. Cycloalkylalkylthio is, for example, (C$_3$-C$_6$)cycloalkyl(C$_1$-C$_6$)alkylthio. Phenylalkoxy is, for example, phenyl(C$_1$-C$_6$)alkoxy such as phenylmethoxy (benzyloxy). Phenylalkylthio is, for example, phenyl(C$_1$-C$_6$)alkylthio. Carboxyalkoxy is, for example, carboxy(C$_1$-C$_6$)alkoxy. Carboxyalkylthio is, for example, carboxy(C$_1$-C$_6$)alkylthio such as carboxymethylthio. Alkoxycarbonylalkoxy is, for example, (C$_1$-C$_6$)alkoxycarbonyl(C$_1$-C$_6$)alkoxy. Alkoxycarbonylalkylthio is, for example, (C$_1$-C$_6$)alkoxycarbonyl(C$_1$-C$_6$)alkylthio such as methoxycarbonylmethylthio or isopropyloxycarbonylmethylthio. Alkanoyl is, for example, (C$_1$-C$_6$)alkanoyl such as acetyl. Alkoxycarbonyl is, for example, (C$_1$-C$_6$)alkoxycarbonyl such as methoxycarbonyl, ethoxycarbonyl, n-propyloxycarbonyl or isopropyloxycarbonyl. Alkenyloxycarbonyl is, for example, (C$_3$-C$_6$)alkenyloxycarbonyl. Alkynyloxycarbonyl is, for example, (C$_3$-C$_6$)alkynyloxycarbonyl. Cycloalkoxycarbonyl is, for example, (C$_3$-C$_6$)cycloalkoxycarbonyl. Cycloalkylalkoxycarbonyl is, for example, (C$_3$-C$_6$)cycloalkyl(C$_1$-C$_6$)alkoxycarbonyl. Alkoxycarbonylalkoxycarbonyl is, for example, (C$_1$-C$_6$)alkoxycarbonyl(C$_1$-C$_6$)alkoxycarbonyl. Hydroxyalkyl is, for example, hydroxy(C$_1$-C$_6$)alkyl such as hydroxymethyl. Alkoxyalkyl is, for example, (C$_1$-C$_6$)alkoxy(C$_1$-C$_6$)alkyl such as methoxymethyl or isopropyloxymethyl. Alkenyloxyalkyl is, for example, (C$_3$-C$_6$)alkenyloxy(C$_1$-C$_6$)alkyl. Alkynyloxyalkyl is, for example, (C$_3$-C$_6$)alkynyloxy(C$_1$-C$_6$)alkyl such as propargyloxymethyl or 1-methylpropargyloxymethyl. Alkylthioalkyl, is for example (C$_1$-C$_6$)alkylthio(C$_1$-C$_6$)alkyl such as isopropylthiomethyl or ethylthiomethyl. Alkenylthioalkyl is, for example, (C$_3$-C$_6$)alkenylthio(C$_1$-C$_6$)alkyl. Alkynylthioalkyl is, for example, (C$_3$-C$_6$)alkynylthio(C$_1$-C$_6$)alkyl. Cycloalkoxyalkyl is, for example, (C$_3$-C$_6$)cycloalkoxy(C$_1$-C$_6$)alkyl. Cycloalkylalkoxyalkyl is, for example, (C$_3$-C$_6$)cycloalkyl(C$_1$-C$_6$)alkoxy(C$_1$-C$_6$)alkyl. Cycloalkylthioalkyl is, for example, (C$_3$-C$_6$)cycloalkylthio(C$_1$-C$_6$)alkyl. Cycloalkylalkylthioalkyl is, for example, (C$_3$-C$_6$)cycloalkyl(C$_1$-C$_6$)alkylthio(C$_1$-C$_6$)alkyl. Alkoxycarbonylalkoxyalkyl is, for example, (C$_1$-C$_6$)alkoxycarbonyl(C$_1$-C$_6$)alkoxy(C$_1$-C$_6$)alkyl such as 1-(ethoxycarbonyl)ethoxymethyl. Phenoxyalkyl is, for example, phenoxy(C$_1$-C$_6$)alkyl such as phenoxymethyl. Phenylthioalkyl is, for example, phenylthio(C$_1$-C$_6$)alkyl such as phenylthiomethyl. Alkylaminoalkyl is, for example, mono(C$_1$-C$_6$)alkylamino(C$_1$-C$_6$)alkyl or di(C$_1$-C$_6$)alkylamino(C$_1$-C$_6$)alkyl such as diisopropylaminomethyl or dimethylaminoethyl. Alkenyl is, for example, (C$_3$-C$_6$)alkenyl such as allyl, 2-chloroallyl or 3,3-dichloroallyl. Alkynyl is, for example, (C$_3$-C$_6$)alkynyl such as propargyl. Alkyloximyl is, for example, (C$_1$-C$_6$)alkyloximyl. Alkenyloximyl is, for example, (C$_3$-C$_6$)alkenyloximyl. Alkynyloximyl is, for example, (C$_3$-C$_6$)alkynyloximyl. Alkoxycarbonylalkyloximyl is, for example, (C$_1$-C$_6$)alkoxycarbonyl(C$_1$-C$_6$)alkyloximyl. Alkyl(alkyl)oximyl is, for example, (C$_1$-C$_6$)alkyl((C$_1$-C$_6$)alkyl)oximyl. Alkenyl(alkyl)oximyl is, for example, (C$_3$-C$_6$)alkenyl((C$_1$-C$_6$)alkyl)oximyl. Alkynyl(alkyl)oximyl is, for example (C$_3$-C$_6$)alkynyl((C$_1$-C$_6$)alkyl)oximyl. Alkoxycarbonylalkyl(alkyl)oximyl is, for example, (C$_1$-C$_6$)alkoxycarbonyl(C$_1$-C$_6$)alkyl((C$_1$-C$_6$)alkyl)oximyl. Alkylamino is, for example, mono(C$_1$-C$_6$)alkylamino or di(C$_1$-C$_6$)alkylamino. Alkenylamino is, for example, mono(C$_3$-C$_6$)alkenylamino. Alkynylamino is, for example, mono(C$_3$-C$_6$)alkynylamino. Alkanoylamino is, for example, mono(C$_1$-C$_6$)alkanoylamino such as acetamido. Alkylsulfonylamino is, for example, (C$_1$-C$_6$)alkylsulfonylamino or di(C$_1$-C$_6$)alkylsulfonylamino such as (dimethylsulfonyl)amino.

In a preferred embodiment of the invention are compounds of the formula

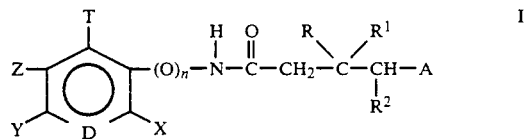

wherein
A is CH$_2$OH, CH$_2$Cl, COOH, COO—M+, (C$_1$-C$_6$)alkoxycarbonyl, or (C$_1$-C$_6$)alkylaminocarbonyl;
n is 0;
D is CH or N;
R is H, (C$_1$-C$_4$)alkyl, halo(C$_1$-C$_4$)alkyl or phenyl;
R$^1$ is H or (C$_1$-C$_2$)alkyl;
R$^2$ is H, (C$_1$-C$_2$)alkyl;
T is H or F;
X is H or halogen; provided that when X and Z are each independently hydrogen or halogen, Y is halogen and D is CH, R must be CF$_3$;
Y is hydrogen, halogen, CF$_3$, OC$_6$H$_5$, cyano or NO$_2$; provided when Y is hydrogen, R is trifluoromethyl (CF$_3$), R$^1$ and R$^2$ are hydrogen and Z is not hydrogen; and when Y is chlorine (Cl) and Z is a substituent linked to the phenyl ring by oxygen, R is not hydrogen; and
Z is H, halogen, (C$_1$-C$_6$)alkoxy, (C$_3$-C$_6$)alkenyloxy, halo(C$_3$-C$_6$)alkenyloxy, (C$_3$-C$_6$)alkynyloxy, (C$_1$-C$_6$)alkylthio, (C$_3$-C$_6$)alkenylthio, (C$_3$-C$_6$)alkynylthio, phenyl(C$_1$-C$_6$)alkoxy, heterocyclyl(C$_1$-C$_6$)alkoxy, phenyl(C$_1$-C$_6$)alkylthio, carboxy(C$_1$-C$_6$)alkylthio, (C$_1$-C$_6$)alkoxycarbonyl(C$_1$-C$_6$)alkylthio, (C$_1$-C$_6$)alkanoyl, (C$_1$-C$_6$)alkoxycarbonyl, (C$_1$-C$_6$)alkyl, hydroxy(C$_1$-C$_6$)alkyl, (C$_1$-C$_6$)alkoxy(C$_1$-C$_6$)alkyl, (C$_3$-C$_6$)alkenyloxy($C_1$-$C_6$)alkyl, ($C_3$-$C_6$)alkynyloxy($C_1$-$C_6$)alkyl, ($C_1$-$C_6$)alkylthio($C_1$-$C_6$)alkyl, ($C_1$-$C_6$)alkoxycarbonyl($C_1$-$C_6$)alkoxy($C_1$-$C_6$)alkyl, phenoxy($C_1$-$C_6$)alkyl, phenylthio($C_1$-$C_6$)alkyl, heterocyclyl, di($C_1$-$C_6$)alkylamino($C_1$-$C_6$)alkyl, mono($C_1$-$C_6$)alkanoylamino, provided when Z is acetamido, Y is not chloro, di($C_1$-$C_6$)alkylsulfonylamino or Y and Z together form a heterocyclic ring fused to the phenyl ring to form a compound of the structure

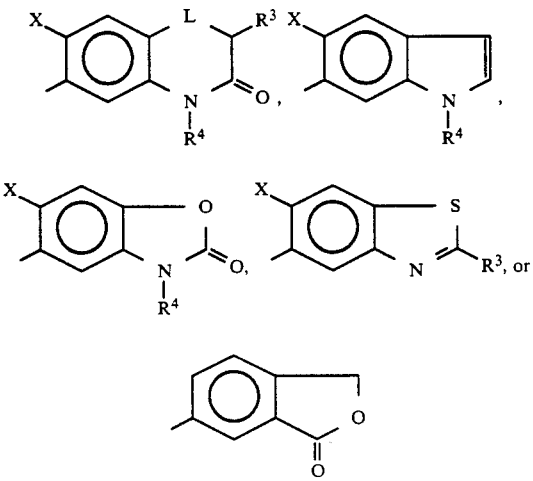

wherein
L is oxygen or sulfur;
$R^3$ is hydrogen or ($C_1$-$C_3$)alkyl;
$R^4$ is hydrogen, ($C_1$-$C_6$)alkyl, ($C_3$-$C_6$)alkenyl, halo($C_3$-$C_6$)alkenyl, ($C_3$-$C_6$)alkynyl, ($C_3$-$C_6$)cycloalkyl($C_1$-$C_6$)alkyl, ($C_1$-$C_6$)alkoxy($C_1$-$C_6$)alkyl, phenyl($C_1$-$C_6$)alkyl, cyano($C_1$-$C_6$)alkyl, heterocyclyl($C_1$-$C_6$)alkyl, ($C_1$-$C_6$)alkylamino($C_1$-$C_6$)alkyl, or ($C_1$-$C_6$)alkoxycarbonyl($C_1$-$C_6$)alkyl.

In one class of the preferred embodiment of the invention are ether and thioether glutaramic acid compounds of Formula I wherein
A is $CO_2H$, ($C_1$-$C_6$)alkoxycarbonyl or $CO_2$—M+;
D is CH or, when X is H, N;
n is 0;
R is ($C_1$-$C_4$)alkyl or halo($C_1$-$C_4$)alkyl;
$R^1$ is H or ($C_1$-$C_2$)alkyl;
$R^2$ is H;
X is H or halogen;
Y is H or halogen;
T is H or F;
Z is H, ($C_1$-$C_6$)alkoxy, ($C_3$-$C_6$)alkenyloxy, halo($C_3$-$C_6$)alkenyloxy, ($C_3$-$C_6$)alkynyloxy, ($C_1$-$C_6$)alkylthio, ($C_3$-$C_6$)alkynyloxy, ($C_1$-$C_6$)alkylthio, ($C_3$-$C_6$)alkenylthio, ($C_3$-$C_6$)alkynylthio, phenyl($C_1$-$C_6$)alkoxy, heterocyclyl($C_1$-$C_6$)alkoxy, phenyl($C_1$-$C_6$)alkylthio, carboxy($C_1$-$C_6$)alkylthio, or ($C_1$-$C_6$)alkoxycarbonyl($C_1$-$C_6$)alkylthio.

Preferred compounds of these glutaramic acid compounds are those of Formula I wherein
A is carboxy, ($C_1$-$C_6$)alkoxycarbonyl or $CO_2$—M+;
D is CH; n is 0; R is $CH_3$, $CF_3$, $CHF_2$ or $CF_2CF_3$; $R^1$ is H; X is Cl or F; Y is Br, F, or Cl; T is H and Z is ($C_1$-$C_6$) alkoxy ($C_3$-$C_6$)alkenyloxy; ($C_3$-$C_6$)alkynyloxy.

More preferably A is carboxy, ethoxycarbonyl, methoxycarbonyl, isopropyloxycarbonyl, ethomeen carboxylate, isopropylammonium carboxylate or potassium carboxylate, X is F, Y is Cl or Br, and Z is propargyloxy, allyloxy, n-propyloxy, isopropyloxy, ethoxy or methoxy.

Most preferably when A is COOH, Y is Cl, and R is $CF_3$, Z is propargyloxy, isopropyloxy, n-propyloxy, ethoxy, methoxy or allyloxy.

Most preferably when A is COOH, Y is Br, and R is $CF_3$, Z is propargyloxy.

Most preferably when R is $CH_3$, Y is Cl, and A is COOH, Z is propargyloxy.

Most preferably when R is $CF_2CF_3$, Y is Cl, and A is COOH, Z is propargyloxy.

Most preferably when R is $CF_3$, Y is Cl, and Z is propargyloxy, A is carboxy, ethoxycarbonyl, methoxycarbonyl, isopropyloxycarbonyl, ethomeen carboxylate, isopropylammonium carboxylate or potassium carboxylate.

Most preferably when R is $CF_3$, Y is Cl, and Z is isopropyloxy, A is carboxy or methoxycarbonyl.

In a second class of the preferred embodiment of the invention are ester glutaramic acid compounds of Formula I wherein
A is carboxy;
D is CH or, when X is H, N;
n is 0;
R is ($C_1$-$C_4$)alkyl or halo($C_1$-$C_4$)alkyl;
$R^1$ is H or ($C_1$-$C_2$)alkyl;
$R^2$ is H;
X is H or halogen;
Y is H or halogen;
T is H or F;
Z is ($C_1$-$C_6$)alkoxycarbonyl.

Preferred compounds of these ester glutaramic acid compounds are compounds of Formula I wherein A is COOH; D is CH; R is $CF_3$ or $CF_2H$; $R^1$ is hydrogen; X is Cl or F; Y is Br, F or Cl; T is H; and Z is ($C_1$-$C_6$)alkoxycarbonyl.

More preferred are the compounds wherein R is $CF_3$ or $CF_2H$; X is F; Y is Cl or Br; and Z is isopropyloxycarbonyl.

Most preferred are the compounds wherein R is $CF_3$, X is F, Y is Cl and Z is isopropyloxycarbonyl; R is $CF_3$, X is F, Y is Br and Z is isopropyloxycarbonyl; and R is $CF_2H$, X is F, Y is Cl and Z is isopropyloxycarbonyl.

In a third class of the preferred embodiment of the invention are alkyl glutaramic acids of Formula I wherein
A is carboxy;
D is CH or, when X is H, N;
n is 0;
R is ($C_1$-$C_4$)alkyl or halo($C_1$-$C_4$)alkyl;
$R^1$ is H or ($C_1$-$C_2$)alkyl;
$R^2$ is H;
X is H or halogen;
Y is H or halogen;
T is H or F;
Z is ($C_1$-$C_6$)alkoxy($C_1$-$C_6$)alkyl, ($C_3$-$C_6$)alkenyloxy($C_1$-$C_6$)alkyl or ($C_3$-$C_6$)alkynyloxy($C_1$-$C_6$)alkyl.

Preferred compounds of these alkyl glutaramic acids are compounds of Formula I wherein A is carboxy; D is CH; n is 0; R is $CF_3$; $R^1$ is hydrogen; X is Cl or F; Y is Br, F or Cl; T is H; and Z is ($C_1$-$C_6$)alkoxy($C_1$-$C_6$)alkyl, ($C_3$-$C_6$)alkenyloxy($C_1$-$C_6$)alkyl or ($C_3$-$C_6$)alkynyloxy($C_1$-$C_6$)alkyl.

More preferably X is F, Y is Cl and Z is isopropyloxymethyl or 1-methylpropargyloxymethyl.

In a fourth class of the preferred compounds of the invention are heterocyclic glutaramic acid compounds of Formula I wherein Y and Z form a heterocyclic ring of the formula

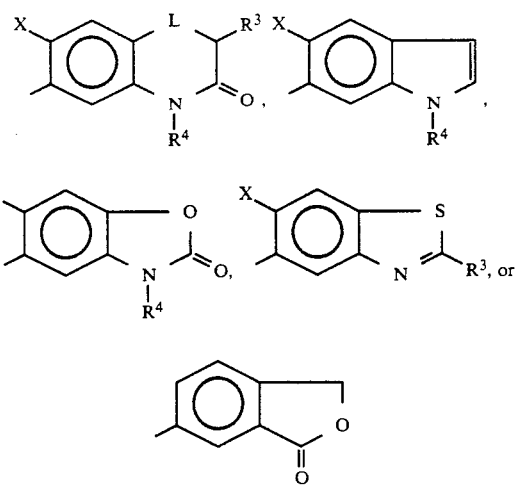

wherein
A is COOH, (C$_1$-C$_6$)alkoxycarbonyl or COO—M+;
D is CH;
n is 0;
L is oxygen or sulfur;
X is hydrogen or fluorine;
R is (C$_1$-C$_4$)alkyl or halo(C$_1$-C$_4$)alkyl;
R$^1$ is H or (C$_1$-C$_2$)alkyl;
R$^2$ is hydrogen;
R$^3$ is hydrogen or (C$_1$-C$_3$)alkyl; and
R$^4$ is hydrogen, (C$_1$-C$_6$)alkyl, (C$_3$-C$_6$)alkenyl, halo(C$_3$-C$_6$)alkenyl, (C$_3$-C$_6$)alkynyl, (C$_3$-C$_6$)cycloalkyl(-C$_1$-C$_6$)alkyl, (C$_1$-C$_6$)alkoxy(C$_1$-C$_6$)alkyl, phenyl(-C$_1$-C$_6$)alkyl, cyano(C$_1$-C$_6$)alkyl, heterocyclyl(C$_1$-C$_6$)alkyl, (C$_1$-C$_6$)alkylamino(C$_1$-C$_6$)alkyl or (C$_1$-C$_6$)alkoxycarbonyl(C$_1$-C$_6$)alkyl.

Preferred compounds of this class of the preferred embodiment are compounds of the formula

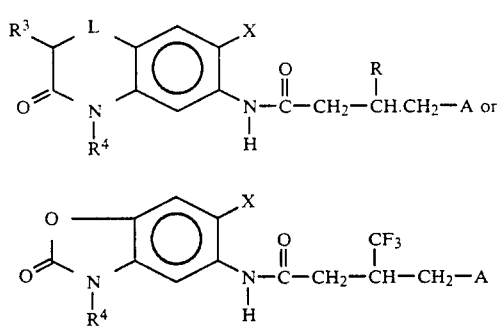

wherein
A is carboxy, COO—M+ or (C$_1$-C$_6$)alkoxycarbonyl;
X is H or F;
L is O or S;
R is CH$_3$, CF$_2$H or CF$_3$;
R$^3$ is H or (C$_1$-C$_3$)alkyl; and
R$^4$ is (C$_1$-C$_6$)alkyl, (C$_3$-C$_6$)alkenyl, halo(C$_3$-C$_6$)alkenyl, (C$_3$-C$_6$)alkynyl, (C$_3$-C$_6$)cycloalkyl(C$_1$-C$_6$)alkyl, (C$_1$-C$_6$)alkoxymethyl, cyano(C$_1$-C$_6$)alkyl, furanyl(-C$_1$-C$_6$)alkyl or phenyl(C$_1$-C$_6$)alkyl.

More preferably when the compound has the structure

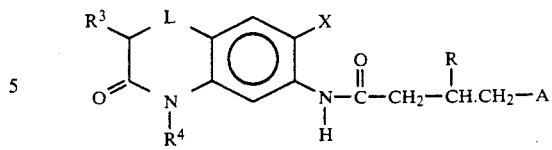

wherein A is carboxy, L is oxygen, X is hydrogen or fluorine, R is CF$_3$ or CHF$_2$ and R$^3$ is methyl, R$^4$ is propargyl; and when A is carboxy or alkoxycarbonyl, L is oxygen, X is hydrogen or fluorine, R is CF$_3$ or CHF$_2$, and R$^3$ is hydrogen, R$^4$ is propargyl, ethyl, allyl, 2-methylallyl, n-propyl, isopropyl, isobutyl, cyanomethyl, ethoxymethyl, methoxymethyl or 2-butenyl.

Most preferably when A is carboxy, L is oxygen, X is hydrogen, R is CF$_3$, and R$^3$ is hydrogen, Z is propargyl, allyl or methoxymethyl.

Most preferably when A is carboxy, L is oxygen, X is fluorine, R is CF$_3$, and R$^3$ is hydrogen, Z is propargyl, ethyl, allyl, 2-methylallyl, 2-chloroallyl, n-propyl, isopropyl, isobutyl, cyclopropylmethyl, cyanomethyl, 2-tetrahydrofuranylmethyl, methoxymethyl, ethoxymethyl or 2-butenyl.

Most preferably when A is methoxycarbonyl or isopropyloxycarbonyl, L is oxygen, X is fluorine, R$^3$ is hydrogen and R$^4$ is allyl.

Most preferably when A is COO—NH$_4$+ or COO—K+, L is oxygen, X is fluorine, R$^3$ is hydrogen and R$^4$ is allyl.

Most preferably when R is CF$_2$H, A is COOH, L is oxygen, X is F, and R$^4$ is propargyl.

More preferably when the compound has the structure

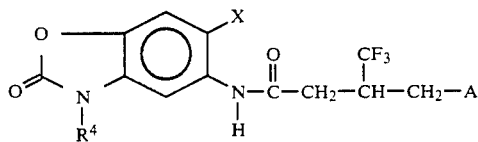

A is COOH, X is hydrogen or fluorine and R$^4$ is propargyl.

The glutaramic acids and derivatives of the instant invention are prepared by starting from an anilino or amino compound of the formula

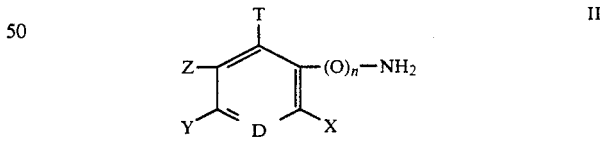

wherein D, T, X, Y, Z, and n are as defined above in Formula I. Compound II is reacted with an equivalent of a suitably substituted glutaric anhydride having the formula

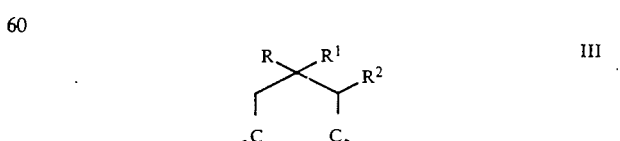

wherein R, R$^1$, and R$^2$ are as defined above in Formula I, to yield a compound having the formula

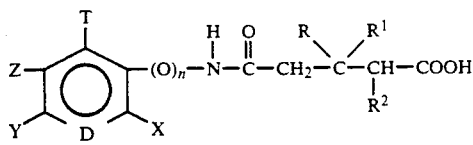

Examples of suitable solvents for this reaction include ethers such as tetrahydrofuran (THF) and glyme, hydrocarbons such as toluene, acetonitrile, N,N-dialkylamides such as dimethylformamide and halocarbons such as methylene chloride and chloroform. The reaction is generally carried out at atmospheric pressure at a temperature of from about −10° C. to about 100° C. Preferably the temperature employed is in the range of from about 0° C. to about 70° C.

The glutaramic acid may then, by means known to one skilled in the art, be reacted with alcohols or amines to form compounds of Formula I where A is an ester or amide. Alternatively the acid functionality is reduced to the primary alcohol (A=$CH_2OH$) and chlorinated using reagents such a thionyl chloride to give compounds of the Formula I where A=$CH_2Cl$.

In the case where Y and Z together form a heterocyclic ring, the amino-substituted heterocycle is prepared by means known in the art and then reacted with the requisite glutaric anhydride (III) as described above.

The starting glutaric anhydrides are prepared as is known in the art, for example, in J. Gootjes and W. Th. Nanto, Rec. Trav. Chem, 80, 1183 (1965). Alternatively, ethyl 4,4,4-trifluorocrotonate and diethyl malonate are reacted in the presence of sodium and a catalytic amount of a catalyst such as tetrabutylammonium bromide to yield ethyl 2-(trifluoromethyl)propanetrioate which is in turn treated with a strong base such as potassium hydroxide, preferably between about 50° C. and about 150° C. then acidified and decarboxylated to yield 3-(trifluoromethyl)glutaric acid.

The starting anilino and amino compounds are prepared as is known to one skilled in the art, as disclosed for example, in U.S. Pat. Nos. 4,439,229, 4,484,940, 4,484,941, 4,594,099, and 4,640,707 and in PCT/EP87/00279 and PCT/US87/0056 and in the references cited therein.

The following examples further illustrate this invention but are not intended to limit it in any way. In Tables I to IV, typical N-substituted glutaramic acids and derivatives are listed with their melting points. The proton NMR data are listed in Table V for those compounds for which no melting point is supplied. Specific illustrative preparations of the compounds are described after Table V.

TABLE I

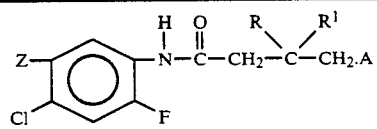

| Cmpd. No. | R | $R^1$ | A | Z | mp (°C.) |
|---|---|---|---|---|---|
| 1. | $CF_3$ | H | $CO_2H$ | OH | 171–174 |
| 2. | $CF_3$ | H | $CO_2H$ | $OCH_3$ | 141–144 |
| 3. | $CF_3$ | H | $CO_2H$ | $OCH_2CH_3$ | 93–95 |
| 4. | $CF_3$ | H | $CO_2H$ | $O(CH_2)_2CH_3$ | 95–98 |
| 5. | $CF_3$ | H | $CO_2H$ | $O(CH_2)_3CH_3$ | 108–111 |
| 6. | $CF_3$ | H | $CO_2H$ | $OCH(CH_3)_2$ | 128–129 |
| 7. | $CF_3$ | H | $CO_2H$ | $OCH(CH_3)CH_2CH_3$ | 96–98 |
| 8. | $CF_3$ | H | $CO_2H$ | $OCH_2CH(CH_3)_2$ | 131–133 |
| 9. | $CF_3$ | H | $CO_2H$ | $OCH_2CH=CH_2$ | 114–116 |
| 10. | $CF_3$ | H | $CO_2H$ | $OCH_2C\equiv CH$ | 140–142 |
| 11. | $CF_3$ | H | $CO_2H$ | $OCH_2C_6H_5$ | 144–146 |
| 12. | $CF_3$ | H | $CO_2CH_3$ | $OCH_2C\equiv CH$ | 103–104 |
| 13. | $CF_3$ | H | $CO_2CH_2CH_3$ | $OCH_2C\equiv CH$ | 88–90 |
| 14. | $CF_3$ | H | $CO_2CH(CH_3)_2$ | $OCH_2C\equiv CH$ | 77–78 |
| 15. | $CF_3$ | H | $CO_2CH(CH_3)_2$ | $OCH(CH_3)_2$ | Oil |
| 16. | $CF_3$ | H | $CO_2{}^-K^+$ | $OCH_2C\equiv CH$ | 172–175 |
| 17. | $CF_3$ | H | $CO_2{}^-NH_3CH(CH_3)_2{}^+$ | $OCH_2C\equiv CH$ | 152–157 |
| 18. | $CF_3$ | H | $CO_2$-EthomeenH$^+$ | $OCH_2C\equiv CH$ | Oil |
| 26. | $CH_3$ | H | $CO_2H$ | $OCH_2C\equiv CH$ | 137–140 |
| 27. | $CH_3$ | $CH_3$ | $CO_2H$ | $OCH_2C\equiv CH$ | 104–105 |
| 28. | $CH_3$ | H | $CO_2H$ | $OCH(CH_3)_2$ | 85–90 |
| 29. | $CF_3$ | H | $CO_2H$ | CHO | 162–164 |
| 31. | $CH_2CH_3$ | H | $CO_2H$ | $OCH_2C\equiv CH$ | 133–136 |
| 32. | $CH_2CH_3$ | H | $CO_2H$ | $OCH(CH_3)_2$ | 104–106 |
| 33. | $CH(CH_3)_2$ | H | $CO_2H$ | $OCH_2C\equiv CH$ | 149–150 |
| 34. | $CH(CH_3)_2$ | H | $CO_2H$ | $OCH(CH_3)_2$ | 127–129 |
| 35. | $CF_2CF_3$ | H | $CO_2H$ | $OCH_2C\equiv CH$ | 115–116 |
| 36. | $CF_2CF_3$ | H | $CO_2H$ | $OCH(CH_3)_2$ | 87–90 |
| 37. | $C_6H_5$ | H | $CO_2H$ | $OCH_2C\equiv CH$ | 142–144 |
| 38. | $CF_3$ | H | $CH_2Cl$ | $OCH(CH_3)_2$ | 57–63 |
| 39. | $CF_3$ | H | $CO_2CH_3$ | $OCH(CH_3)_2$ | 53–56 |
| 45. | $CF_3$ | H | $CH_2OH$ | $OCH(CH_3)_2$ | Oil |
| 51. | $CF_3$ | H | $CO_2H$ | $CO_2CH(CH_3)_2$ | 127–129 |
| 52. | $CF_3$ | H | $CO_2H$ | $SCH_2CO_2H$ | 142–145 |
| 53. | $CF_3$ | H | $CO_2CH_3$ | $SCH_2CO_2CH_3$ | 72–75 |
| 54. | $CF_3$ | H | $CO_2H$ | $SCH_2CO_2CH_3$ | 99–103 |
| 55. | $CF_3$ | H | $CO_2H$ | $CO_2CH_3$ | 138–139 |
| 56. | $CF_3$ | H | $CO_2CH_3$ | $CO_2CH_3$ | 95–97 |
| 57. | $CF_3$ | H | $CO_2H$ | $SCH_3$ | 138–140 |

TABLE I-continued

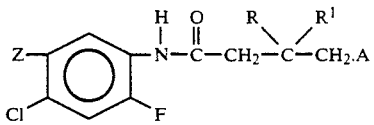

| Cmpd. No. | R, | R¹ | A | Z | mp (°C.) |
|---|---|---|---|---|---|
| 58. | $CF_3$ | H | $CO_2H$ | $CO_2CH_2CH_3$ | 138-140 |
| 59. | $CF_3$ | H | $CO_2H$ | $CO_2(CH_2)_2CH_3$ | 139-141 |
| 60. | $CF_3$ | H | $CO_2H$ | $SCH(CH_3)_2$ | 73-74 |
| 61. | $CF_3$ | H | $CO_2CH(CH_3)_2$ | $CO_2CH(CH_3)_2$ | 101-102 |
| 62. | $CF_3$ | H | $CO_2H$ | $SCH_2CO_2CH(CH_3)_2$ | 135-137 |
| 63. | $CF_3$ | H | $CO_2H$ | $CH_2OH$ | 151.5-153 |
| 66. | $CF_3$ | H | $CO_2H$ | $CH_2OCH_3$ | 125.5-127.5 |
| 67. | $CF_3$ | H | $CO_2H$ | $CH_2OCH(CH_3)_2$ | 120.5-122.5 |
| 68. | $CF_3$ | H | $CO_2H$ | $CH_2OCH_2C\equiv CH$ | 95-97 |
| 72. | $CF_3$ | H | $CO_2H$ | $CH_2SCH(CH_3)_2$ | 129-130.5 |
| 73. | $CF_3$ | H | $CO_2H$ | $CH_2SCH_2CH_3$ | 115-116.5 |
| 74. | $CF_3$ | H | $CO_2H$ | $CH_2SC_6H_5$ | 95-101 |
| 75. | $CF_3$ | H | $CO_2H$ | $CH_2OC_6H_5$ | 137-140 |
| 76. | $CF_3$ | H | $CO_2H$ | $CH_2OCH(CH_3)CO_2C_2H_5$ | Oil |
| 80. | $CF_3$ | H | $CO_2H$ | $CH_2N(CH(CH_3)_2)_2$ | 138-141 |
| 81. | $CF_3$ | H | $CO_2H$ | $CH_3$ | 150-151 |
| 94. | $CF_3$ | H | $CO_2H$ | $OCH_2CH_2C\equiv CH$ | 136-137 |
| 95. | $CF_3$ | H | $CO_2H$ | $OCH(CH_3)C\equiv CH$ | 87-90 |
| 96. | $CF_3$ | H | $CO_2H$ | $CH_2OCH(CH_3)C\equiv CH$ | 128-130 |
| 98. | $CF_3$ | H | $CO_2H$ | $COCH_3$ | 107-109 |
| 115. | $CF_3$ | H | $CO_2H$ | $OCH_2OCH_3$ | 78-80 |
| 119. | $CF_3$ | H | $CO_2^-K^+$ | $CO_2^-K^+$ | dec |
| 123. | $CH_2F$ | H | $COOH$ | $OCH_2C\equiv CH$ | |
| 127. | $CF_3$ | H | $CO_2H$ |  | 126-127 |
| 128. | $CH_3$ | H | $CO_2H$ | $CO_2CH(CH_3)_2$ | 120.5-122 |
| 130. | $CF_3$ | H | $CO_2H$ | $SCH_2CH(CH_3)_2$ | 108-111 |
| 140. | $CF_3$ | H | $CO_2H$ | 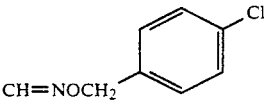 | 169-171 |
| 141. | $CH_2F$ | H | $COOH$ | $CO_2CH(CH_3)_2$ | |
| 142. | $CF_3$ | H | $CO_2H$ | $NO_2$ | 140-142 |
| 144. | $CF_3$ | H | $CO_2H$ | $NH_2$ | 62-64 |
| 148. | $CF_3$ | H | $CO_2H$ | 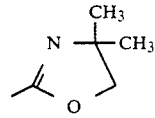 | 162-165 |
| 150. | $CF_3$ | H | $CO_2H$ | 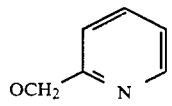 | 167-168.5 |
| 151. | $CF_3$ | H | $CO_2H$ | 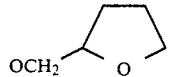 | 103-106 |
| 153. | $CF_3$ | H | $CO_2H$ | 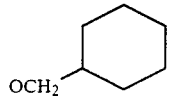 | 66-70 |
| 155. | $CF_3$ | H | $CO_2H$ | $OSO_2CH_3$ | 153-156 |
| 156. | $CF_2H$ | H | $CO_2H$ | $CO_2CH(CH_3)_2$ | 122-123 |
| 158. | $CF_3$ | H | $CO_2H$ | $OCH_2C(Cl)=CH_2$ | 92-95 |
| 159. | $CF_2H$ | H | $CO_2H$ | $OCH_2C\equiv CH$ | 88-91 |
| 160. | $CF_3$ | H | $CO_2H$ | $OCH_2CH=C(Cl)_2$ | 117-118.5 |

TABLE I-continued

Structure: Z-substituted, Cl and F on phenyl ring, N-H, C(=O)-CH₂-C(R)(R¹)-CH₂.A

| Cmpd. No. | R | R¹ | A | Z | mp (°C.) |
|---|---|---|---|---|---|
| 163. | CF₃ | H | CO₂H | S(O)CH₂CH(CH₃)₂ | 110–115 |

TABLE II

Structure: phenyl with substituents T, X, Y, Z, D, (O)ₙ, connected to N-H, C(=O)-CH₂-C(R)(R¹)-CH(R²)-A

| Cmpd. No. | R, R¹ | R² | A | D | n | T | X | Y | Z | mp (°C.) |
|---|---|---|---|---|---|---|---|---|---|---|
| 19. | CF₃, H | H | CO₂H | CH | 0 | H | H | Cl | OCH₂C≡CH | 149–150 |
| 20. | CF₃, H | H | CO₂H | CH | 0 | H | Cl | Cl | OCH₂C≡CH | 148–152 |
| 21. | CF₃, H | H | CO₂H | CH | 0 | H | F | F | H | 127–131 |
| 22. | CF₃, H | H | CO₂H | CH | 0 | F | F | F | H | 151.5–153.5 |
| 23. | CF₃, H | H | CO₂H | CH | 0 | H | F | Br | H | 162–164 |
| 24. | CF₃, H | H | CO₂H | CH | 0 | H | H | Br | H | 173–176 |
| 25. | CF₃, H | H | CO₂H | CH | 0 | H | H | Cl | Cl | 178–180 |
| 30. | CH₃, H | H | CO₂H | CH | 0 | H | Cl | Cl | OCH₂C≡CH | 148–152 |
| 40. | CH₃, H | H | CO₂H | CH | 0 | H | H | CF₃ | H | 134–137 |
| 41. | H, H | CH₃ | CO₂H | CH | 0 | H | H | Br | H | 127–128 |
| 42. | CH₃, H | H | CO₂H | CH | 0 | H | H | Cl | OCH₂C≡CH | 128–130 |
| 43. | H, H | H | CO₂H | CH | 0 | H | H | OC₆H₅ | H | 140–142 |
| 44. | CF₃, H | H | CO₂H | N | 0 | H | H | Cl | H | 166–168.5 |
| 46. | CF₃, H | H | CO₂H | CH | 1 | H | H | NO₂ | CO₂CH₃ | 118–121 |
| 47. | CF₃, H | H | CO₂H | CH | 1 | H | H | Cl | H | 120–125 |
| 48. | CF₃, H | H | CO₂CH₃ | CH | 0 | H | F | Br | H | 93–99 |
| 49. | CF₃, H | H | CO₂C₂H₅ | CH | 0 | H | F | Br | H | 118–120 |
| 50. | CF₃, H | H | CO₂CH(CH₃)₂ | CH | 0 | H | F | Br | H | 120–121 |
| 64. | CF₃, H | H | CO₂H | CH | 0 | H | Cl | Cl | CO₂CH(CH₃)₂ | 152.5–154 |
| 65. | CH₃, H | H | CO₂H | CH | 0 | H | F | Br | H | 145–147 |
| 88. | CF₃, H | H | CO₂H | CH | 0 | H | H | Cl | N(SO₂CH₃)₂ | 204–207 |
| 100. | CF₃, H | H | CO₂H | CH | 0 | H | H | CN | H | 110–111 |
| 101. | CF₃, H | H | CO₂H | CH | 0 | H | H | OCH₃ | NHCOCH₃ | 165–167 |
| 104. | CF₃, H | H | CO₂CH₃ | CH | 0 | H | F | H | CO₂CH(CH₃)₂ | 83–85 |
| 111. | CF₃, H | H | CO₂H | CH | 0 | H | F | H | CO₂CH(CH₃)₂ | 139–140 |
| 124. | CF₃, H | H | CO₂H | CH | 0 | H | H | NO₂ | H | 103–104 |
| 126. | CF₃, H | H | CO₂H | CH | 0 | H | H | CF₃ | H | 138–139 |
| 133. | CF₃, H | H | CO₂H | CH | 0 | H | F | Br | CO₂CH(CH₃)₂ | 125–130 |
| 134. | CF₃, H | H | CO₂H | CH | 0 | H | H | Cl | CO₂CH(CH₃)₂ | 100–102 |
| 135. | CF₃, H | H | CO₂H | CH | 0 | H | F | F | F | 149.5–151.5 |
| 138. | CF₃, H | H | CO₂H | CH | 0 | H | F | F | OCH₂C≡CH | 84–85 |
| 143. | CF₃, H | H | CO₂H | CH | 0 | H | F | F | CO₂CH(CH₃)₂ | 145–147 |
| 145. | CF₃, H | H | CO₂H | CH | 0 | H | F | Br | OCH₂C≡CH | 127–128 |

TABLE III

Structure: phenyl with L, X, R³, R⁴ on one side (R³-CH-C(=O)-N(R⁴)-); other side N-H, C(=O)-CH₂-CH(R)-CH₂-A

| Cmpd. No. | L | X | R | R³ | R⁴ | A | mp (°C.) |
|---|---|---|---|---|---|---|---|
| 69. | O | H | CF₃ | CH₃ | CH₂C≡CH | CO₂H | 139–141 |
| 70. | O | H | CF₃ | H | CH₂C≡CH | CO₂H | 158–159 |
| 77. | O | H | CH₃ | H | CH₂C≡CH | CO₂H | 97–100 |
| 78. | O | F | CH₃ | H | CH₂C≡CH | CO₂H | 143–144.5 |
| 79. | O | F | CF₃ | H | CH₂C≡CH | CO₂H | 167–170 |
| 82. | O | F | CF₃ | H | CH₂CH₂CH₃ | CO₂H | 151–153 |
| 83. | O | F | CF₃ | H | CH₂CH=CH₂ | CO₂H | 171–172 |
| 84. | S | H | CF₃ | H | CH₂C≡CH | CO₂H | 103–105 |
| 86. | O | F | CF₃ | H | CH₂C₆H₅ | CO₂H | 214–218 |
| 87. | O | F | CF₃ | H | CH₂CH(CH₃)₂ | CO₂H | 176–178 |

TABLE III-continued

| Cmpd. No. | L | X | R | R³ | R⁴ | A | mp (°C.) |
|---|---|---|---|---|---|---|---|
| 89. | O | F | $CF_3$ | H | $CH_3$ | $CO_2H$ | 189-193 |
| 90. | O | F | $CF_3$ | H | $CH_2CN$ | $CO_2H$ | 115-120 |
| 91. | O | F | $CF_3$ | H | H | $CO_2H$ | 228-230 |
| 92. | O | F | $CF_3$ | H | $CH_2CO_2CH(CH_3)_2$ | $CO_2H$ | 158-161 |
| 93. | O | F | $CF_3$ | H | $CH_2OCH_2CH_3$ | $CO_2H$ | 170-173 |
| 97. | O | F | $CF_3$ | H | $CH(CH_3)_2$ | $CO_2H$ | 120-123 |
| 99. | O | H | $CF_3$ | H | $CH(CH_3)C\equiv CH$ | $CO_2H$ | 53-54 |
| 102. | O | F | $CF_3$ | H | $CH(CH_3)CN$ | $CO_2H$ | Oil |
| 105. | O | H | $CF_3$ | H | $CH_2CH=CH_2$ | $CO_2H$ | 158-159.5 |
| 106. | O | F | $CF_3$ | H | $CH_2CH=CHCH_3$ | $CO_2H$ | 170-172 |
| 107. | O | F | $CF_3$ | H | $CH_2C(CH_3)=CH_2$ | $CO_2H$ | 180-182 |
| 108. | O | F | $CF_3$ | H | $CH_2CH_3$ | $CO_2H$ | 170-174 |
| 109. | O | F | $CF_3$ | H | $CH_2CH_2CH_2CH_3$ | $CO_2H$ | 175-176 |
| 110. | O | F | $CF_3$ | H | $CH_2CH=CH_2$ | $CO_2CH_3$ | 119-121 |
| 112. | O | F | $CF_3$ | H | $CH_2CH=CH_2$ | $CO_2CH(CH_3)_2$ | 139-140 |
| 113. | O | H | $CF_3$ | H | $CH_2OCH_3$ | $CO_2H$ | 120-122 |
| 116. | O | F | $CF_3$ | H | $CH_2CH=CH_2$ | $CO_2^-NH_4^+$ | 150-153 |
| 117. | O | F | $CF_3$ | H | $CH_2CH=CH_2$ | $CO_2^-K^+$ | 149-152 |
| 120. | O | F | $CF_3$ | H | $CH_2$-cyclopropyl | $CO_2H$ | 155-156 |
| 121. | O | F | $CF_3$ | H | $CH_2C(=O)CH_3$ | $CO_2H$ | |
| 122. | S | F | $CF_3$ | H | $CH_2CH=CH_2$ | $CO_2H$ | 163-164 |
| 125. | O | F | $CF_3$ | H | cyclopentyl | $CO_2H$ | foam |
| 129. | O | H | $CF_3$ | H | $CH_2CH_2CH_3$ | $CO_2H$ | 160-161 |
| 131. | O | F | $CF_3$ | H | $CH_2$-cyclohexyl | $CO_2H$ | 184-185 |
| 132. | O | F | $CF_3$ | H | $CH_2$-(tetrahydrofuran-2-yl) | $CO_2H$ | 149-150 |
| 136. | O | F | $CH_2F$ | H | $CH_2C\equiv CH$ | $CO_2H$ | |
| 137. | O | F | $CF_3$ | H | $CH_2$-(tetrahydrofuran-3-yl) | $CO_2H$ | Oil |
| 139. | O | F | $CH_2F$ | H | $CH_2CH=CH_2$ | $CO_2H$ | |
| 141. | O | H | $CF_3$ | H | $CH_2CH_2OH$ | $CO_2H$ | 170-173 |
| 146. | O | F | $CF_3$ | H | $CH_2CH_2N(CH_3)_2$ | $CO_2H$ | 128-130 dec |
| 147. | O | F | $CF_3$ | H | $CH_2OCH_3$ | $CO_2H$ | 132-135 |
| 149. | O | F | $CF_3$ | H | $CH_2C(CO)=CH_2$ | $CO_2H$ | 190-192 |
| 152. | O | F | $CF_3$ | H | $CH_2CH=C(Cl)_2$ | $CO_2H$ | 187-189 |
| 154. | O | F | $CF_3$ | $CH_2CH_3$ | $CH_2C\equiv CH$ | $CO_2H$ | 148-150 |
| 157. | O | F | $CF_2H$ | H | $CH_2C\equiv CH$ | $CO_2H$ | 165-167 |
| 161. | O | F | $CF_3$ | H | $CH_2CH=CH_2$ | $CH_2OH$ | Oil |
| 162. | O | F | $CF_3$ | H | $CH_2CH(OH)CH_2$ | $CO_2H$ | 148-151 |

TABLE IV
HETEROCYCLIC COMPOUNDS

| Comp. No. | Structure | m.p. °C. |
|---|---|---|
| 71. | (benzofuran-type ring with N-CH₂C≡CH substituent)—NH—C(=O)—CH₂—CH(CF₃)CH₂—COOH | 194–196 |
| 85. | (benzothiazoline-type: H₃C—C(=S)—N on ring)—NH—C(=O)—CH₂—CH(CF₃)CH₂—COOH | 234–236 |
| 103. | (phthalide-type ring)—NH—C(=O)—CH₂—CH(CF₃)CH₂—COOH | 190–192 |
| 114. | (indole ring with N-CH(CH₃)₂)—NH—C(=O)—CH₂—CH(CF₃)CH₂—COOH | 158–160 |
| 118. | (benzoxazinone-type ring with N-CH₂CH₂CH₃)—NH—C(=O)—CH₂—CH(CF₃)CH₂—COOH | 173–176 |

TABLE V
NMR DATA

| Cmpd. No. | Solvent | (200 MHz, delta Scale in ppm TMS Standard) |
|---|---|---|
| 15. | d₆-acetone | 1.2(d,6H), 1.4(d,6H), 2.5–3.0(m,4H), 3.4(m,1H), 4.5(heptet,1H), 5.0(heptet,1H), 7.2 (d,1H), 8.1(d,1H), 9.2(bs*,1H) |
| 18. | d₆-acetone | 0.9(m,3H), 1.2–1.4(m,20H), 1.5(m,2H), 2.3–2.6(m,4H), 2.6–3.0(m,4H), 3.13(t,1H), 3.3(m,1H), 3.48–4.0(m,17H), 4.55(bs,2H), 4.85(d,2H), 7.30(d,1H), 8.34(d,1H), 10.0(bs,1H) |
| 45. | CDCl₃ | 1.4(d,6H), 1.7(m,1H), 2.1(m,1H), 2.5–2.9(m,3H), 3.05(m,1H), 3.8(m,2H), 4.55(heptet,1H), 7.15(d,1H), 7.82(bs,1H), 8.05(d,1H) |
| 76. | CDCl₃ + 2 drops d₆-acetone | 1.33(t,3H), 2.55–2.85(m,4H), 3.25–3.45(m,1H), 4.11(q,1H), 4.26(q,2H), 4.52(A of AB,1H), 4.70(B of AB,1H), 7.14(d,1H), 8.36(d,1H), 8.79(bs,1H) |
| 102. | d₆-acetone | 1.8(d,3H), 2.8(m,2H), 3.0(bm**,2H), 3.6(bm,1H), 4.8(s,2H), 6.1(q,1H), 8.4(d,1H), 9.2(bs,1H) |
| 161. | d₆-acetone | 1.7(m,1H), 2.0(m,1H), 2.8(m,4H), 3.1(m,1H), 3.2(s,b,1H), 4.5(d,2H), 4.5(s,1H), 5.2(m,2H), 5.9(m,1H), 6.9(d,1H), 8.0(d,1H), 9.3,b,1H) |

*bs = broad singlet
**bm = broad multiplet

EXAMPLE A

Preparation of 4-chloro-2-fluoro-5-propargyloxyaniline

Into a 300 milliliter (ml), three-necked round-bottomed flask equipped with an overhead stirrer, dropping funnel and thermometer were placed 5-acetamido-2-chloro-4-fluorophenol (21.0 gram (g), 0.103 mole) and dimethyl sulfoxide (DMSO) (100 ml). The mixture was stirred at room temperature and aqueous potassium hydroxide (KOH) (7.0 g KOH, 88% w/w, 1.01 equivalents (eq) dissolved in 10 ml H₂O) was added dropwise over 10 minutes. An exotherm was noted (25° to 40° C.) during the addition. The solution was stirred for 1 hour, and then a solution of propargyl bromide (80% in toluene, 12.7 ml, 1.10 eq) was added dropwise. An exotherm from 25° to 40° C. was noted during addition. The mixture was stirred at ambient temperature overnight.

In the morning, thin layer chromatography (TLC) (silica gel, 1:1 v/v hexanes/ethyl acetate (EtOAc)) showed that the reaction was complete. The mixture was poured into ice water (600 ml), filtered, washed with water and dried in vacuo at 50° C. overnight to give the expected propargyloxyacetanilide as a tan powder (24.0 g, 96%, m.p. 142°–5° C.).

Into a 250 ml, three-necked round-bottomed flask equipped with an overhead stirrer, thermometer and condenser were placed the propargyloxyacetanilide (9.64 g, 40 mmol), ethanol (absolute, 43 ml), water (56 ml) and concentrated aqueous hydrochloric acid (HCl) (35% w/w, 37.5 ml). A heating mantle was used to heat the mixture to reflux with stirring. After 1 hour at reflux (92° C.), TLC (silica gel, 3:1 hexanes/EtOAc, v/v) of a basified aliquot indicated that the reaction was complete. The mixture was poured into ice water (200 ml) and brought to pH 10 using 50% aq. sodium hydroxide (NaOH) (25 ml) during which time a brown solid precipitated. The mixture was extracted with ether (3×100 ml) and the combined organic layers were washed (2×50 ml water, 1×50 ml brine), and dried over anhydrous magnesium sulfate (MgSO$_4$). The mixture was filtered, the solvent evaporated in vacuo and dried overnight at 25° C. to give the expected aniline as a brown oil.

EXAMPLE B 3-(trifluoromethyl)glutaric anhydride

To 115 mg (5 mmol) of sodium metal (cut into small pieces and washed with hexanes) in 5 ml of THF was added a solution of diethyl malonate (800 mg, 5 mmol) in 10 ml THF. The mixture was stirred at room temperature until all of the sodium metal was consumed (2-3 hours). A catalytic amount of tetrabutylammonium bromide was added, followed by a THF solution (10 ml) of ethyl 4,4,4-trifluorocrotonate (0.84 g, 5 mmol). This mixture was warmed to 40° C. and stirred for 17 hours. After cooling to 10° C., glacial acetic acid (300 mg, 5 mmol) was added and the THF was removed in vacuo. The resulting residue was treated with a solution of 87.3% KOH (1.28 g, 20 mmol) in 10 ml water and refluxed for 4.5 hours. After cooling to 10° C., 2.5 ml (26 mmol) of conc. HCl was added dropwise via pipette and the mixture was again heated to reflux until CO$_2$ evolution had ceased (ca. 1 hour). The solution was cooled to 15° C. and extracted with Et$_2$O(3×10 ml). The combined organic phases were dried over Na$_2$SO$_4$, filtered and concentrated in vacuo to afford 3-(trifluoromethyl)glutaric acid as a white solid in 95% yield (m.p. 100°-100.5° C.).

Into a 2 liter 3-necked flask equipped with a mechanical stirrer and reflux condenser were added 320 g (1.6 mol) 3-(trifluoromethyl)glutaric acid and 775 ml acetic anhydride. The solution was refluxed for 2.5 hours and allowed to cool to room temperature. The majority of the acetic anhydride was removed in vacuo (80° C.) to afford a brown solid which was dissolved in 800 ml of CHCl$_3$ on a steam bath. Following the addition of 200 ml hexanes, a white precipitate began to form. Further crystallization was induced by storage in a refrigerator. The white flocculent solid was filtered and oven dried (50° C., 30 mm Hg) to afford 261 g (89% yield) of the desired product, m.p. 88°-91° C.

EXAMPLE 1

N-(4'-chloro-2'-fluoro-5'-hydroxyphenyl)-3-(trifluoromethyl)glutaramic acid (Compound 1)

Into a 1 liter, three-necked round-bottomed flask equipped with a magnetic stir bar, thermometer, dropping funnel, condenser and N$_2$ inlet were placed 4-chloro-2-fluoro-5-hydroxyaniline (25.7 g, 0.159 mol), water (24 ml), acetic acid (8.4 ml) and tetrahydrofuran (THF) (48 ml). The mixture was stirred to homogeneity, then heated to 40° C. and a solution of 3-(trifluoromethyl)glutaric anhydride (34.8 g, 0.191 mol) in THF (60 ml) was added dropwise via an addition funnel and an exotherm of about 3°-4° C. was noted. The resulting mixture was heated to 50° C. for three hours then cooled to ambient temperature.

The reaction mixture was poured onto 600 ml of ice. When the ice melted, the solid was isolated via suction filtration through a coarse sintered glass funnel. The solid was washed well with water and dried in vacuo at 50° C. to yield the glutaramic acid as a grey solid (51.91 g, 95% yield, m.p. 171°-174° C.).

EXAMPLE 2

N-(4'-chloro-2'-fluoro-5'-propargyloxyphenyl)-3-(trifluoromethyl)glutaramic acid (Compound 10)

Into a 1 liter three-necked round-bottomed flask equipped with overhead stirrer, dropping funnel, thermometer and nitrogen (N$_2$) inlet were placed 3-(trifluoromethyl)glutaric anhydride (18.2 g, 0.100 mol) and methylene chloride (CH$_2$Cl$_2$) (250 ml). The mixture was stirred to homogeneity and a solution of 4-chloro-2-fluoro-5-propargyloxyaniline (19.9 g, 0.100 mol) in CH$_2$Cl$_2$ (50 ml) was added dropwise over 10 minutes to give a clear solution. The mixture was stirred overnight at ambient temperature, during which time a thick white precipitate was formed.

In the morning, the reaction mixture was vacuum filtered and washed sparingly with CH$_2$Cl$_2$ to provide the glutaramic acid as a white solid, 36.6 g (96% yield), m.p. 140°-2° C.

Using the same procedures as described in Example 2, Compounds 2-9, 11, 19-25, 29, 44, 46, 47, 51, 52, 54, 55, 57-60, 62-64, 66-68, 72-76, 80, 81, 85, 88, 96, 98, 100, 103, 111, 124, 126, 127, 130, 133-135, 138, 143, 145 and 158 as defined in Tables I, II and IV were prepared except the anilino or amino compound (Formula II) was: 4-chloro-2-fluoro-5-methoxyaniline, 4-chloro-2-fluoro-5-ethoxyaniline, 4-chloro-2-fluoro-5-n-propyloxyaniline, 4-chloro-2-fluoro-5-n-butyloxyaniline, 4-chloro-2-fluoro-5-isopropyloxyaniline, 4-chloro-2-fluoro-5-s-butyloxyaniline, 4-chloro-2-fluoro-5-isobutyloxyaniline, 4-chloro-2-fluoro-5-allyloxyaniline, 5-benzyloxy-4-chloro-2-fluoroaniline, 2,4,6-trifluoroaniline, 4-bromo-2-fluoroaniline, 2,4-difluoroaniline, 2,4-dichloroaniline, 4-chloro-3-propargyloxyaniline, 2,4-dichloro-5-propargyloxyaniline, 5-amino-2-chloropyridine, 4-chloro-2-fluoro-5-(isopropylthio)aniline, 4-chloro-2-fluoro-5-[(isopropyloxycarbonyl)methylthio]aniline, isopropyl 5-amino-2-chloro-4-fluorobenzoate, 4-chloro-2-fluoro-5-[(methoxycarbonyl)methylthio]aniline, 4-chloro-2-fluoro-5-[(carboxy)methylthio]aniline, 4-chloro-2-fluoro-5-(methylthio)aniline, methyl 5-amino-2-chloro-4-fluorobenzoate, 4-chlorophenoxyamine, 3-methoxycarbonyl-4-nitrophenoxyamine, ethyl 5-amino-2-chloro-4-fluorobenzoate, n-propyl 5-amino-2-chloro-4-fluorobenzoate, 4-chloro-2-fluoro-5-hydroxymethylaniline, isopropyl 5-amino-2,4-dichlorobenzoate, 4-chloro-2-fluoro-5-methoxymethylaniline, 4-chloro-2-fluoro-5-[(isopropyloxy)methyl]aniline, 4-chloro-2-fluoro-5-[(propargyloxy)methyl]aniline, 5-amino-2-chloro-4-fluorotoluene, 5-amino-2-chloro-4-fluorobenzaldehyde, 4-bromoaniline, 5-amino-2-methylbenzothiazole, 4-chloro-2-fluoro-5-(isopropylthiomethyl)aniline, 4-chloro-2-fluoro-5-(ethylthiomethyl)aniline, 4-chloro-2-fluoro-5-(phenoxymethyl)aniline, 4-chloro-2-fluoro-5-(phenylthiomethyl)aniline, 4-chloro-2-fluoro-5-[(1-ethoxycarbonyl)ethoxymethyl]aniline, 4-chloro-2-fluoro-5-[(3-butynyl-2-oxy)methyl]aniline, isopropyl 3-amino-4-fluorobenzoate, 4-chloro-2-fluoro-5-[(N,N-diisopropylamino)methyl]aniline, 4-chloro-3-(N,N-bis-(methylsulfonyl)amino)aniline, 6-aminophthalide, 4-aminobenzonitrile, 5-amino-2-chloro-4-fluoroacetophenone, 4-nitroaniline, 4-(trifluoromethyl)aniline, 4-chloro-5-cyclopentyloxy-2-fluoroaniline, 4-chloro-2-fluoro-5-(isobutylthio)aniline, isopropyl 5-amino-2-bromo-4-fluorobenzoate, isopropyl 5-amino-2-chlorobenzoate, 2,4,5-trifluoroaniline, 2,4-difluoro-5-propargyloxyaniline, isopropyl 5-amino-2,4-difluorobenzoate, 4-bromo-2-fluoro-5-propargyloxyaniline or 4-chloro-5-(2-chloroallyloxy)-2-fluoroaniline.

In addition, the procedure of Example 2 was used to prepare Compounds 26, 27, 28, 31–37, 40, 41, 43, 65, 128 and 156 as described in Table I except the appropriate glutaric anhydride of Formula III, i.e., 3-methylglutaric anhydride, 3-ethylglutaric anhydride, 3,3-dimethylglutaric anhydride, 2-methylglutaric anhydride, glutaric anhydride, 3-(pentafluoroethyl)glutaric anhydride, 3-isopropylglutaric anhydride, 3-(difluoromethyl)glutaric anhydride or 3-phenylglutaric anhydride was reacted with an anilino compound (Formula II): 4-chloro-2-fluoro-5-isopropyloxyaniline, 4-chloro-2-fluoro-5-propargyloxyaniline, 4-bromo-2-fluoroaniline, 4-(trifluoromethyl)aniline, 4-bromoaniline, isopropyl 5-amino-2-chloro-4-fluorobenzoate or 4-phenoxyaniline.

EXAMPLE 3

Methyl N-(4'-chloro-2'-fluoro-5'-propargyloxyphenyl)-3-(trifluoromethyl)glutaramate (compound 12)

To a stirred solution of N-(4'-chloro-2-fluoro-5'-propargyloxyphenyl)-3-(trifluoromethyl)glutaramic acid (1.99 g, 5.24 mmol) in methanol was added distilled thionyl chloride (0.57 ml, 7.8 mmol) via syringe. The mixture was stirred at room temperature overnight then poured onto about 100 ml ice. The resulting mixture was extracted with ethyl ether (1×75 ml) and the organic layer was separated, dried over magnesium sulfate, and the solvent was removed in vacuo to yield 1.87 g (91% yield) of off-white solid (m.p. 103°–4° C.).

Using the same procedure, Compounds 39, 48, 53, 56, 110 and 104 were prepared starting from the appropriate glutaramic acid.

Using ethanol or isopropanol in place of methanol, the same procedure was used to prepare Compounds 13, 14, 15, 49, 50, 61 and 112.

EXAMPLE 4

Isopropyl amine salt of N-(4'-chloro-2'-fluoro-5'-propargyloxyphenyl)-3-(trifluoromethyl)glutaramic acid (Compound 17)

A mixture of N-(4'-chloro-2'-fluoro-5'-propargyloxyphenyl)-3-(trifluoromethyl)glutaramic acid (0.50 g, 1.3 mmol), isopropyl amine (0.11 ml, 1.3 mmol) and 1.5 ml of methanol was stirred at room temperature for about 2 hours. The solvent was removed in vacuo to yield 0.53 g (92% yield) of an off-white solid (m.p. 152°–7° C.).

EXAMPLE 5

Ethomeen C/15 salt of N-(4'-chloro-2'-fluoro-5'-propargyloxyphenyl)-3-(trifluoromethyl)glutaramic acid (Compound 18)

A mixture of N-(4'-chloro-2'-fluoro-5'-propargyloxyphenyl)-3-(trifluoromethyl)glutaramic acid (0.50 g, 1.3 mmol) and Ethomeen C/15 (1.12 g) was stirred at room temperature for 3–4 hours to yield 1.2 g of oil. Ethomeen is $CH_3(CH_2)_{11}N((OCH_2CH_2)_xOH)((OCH_2CH_2)_yOH)$ (x+y=5).

EXAMPLE 6

N-(4'-chloro-2'-fluoro-5'-isopropyloxyphenyl)-5-chloro-3-(trifluoromethyl)pentanamide (Compound 38)

To a solution of N-(4'-chloro-2'-fluoro-5'-isopropyloxyphenyl)-5-hydroxy-3-(trifluoromethyl)pentanamide (1.2 g, 3.2 mmol) (Compound 45) in methylene chloride (100 ml), was added thionyl chloride (0.24 ml) in one portion via pipette. The solution turned brown. The reaction mixture was heated to 40°–50° C. for 7 hours, kept at room temperature for 64 hours, heated to 40° C. for 3 hours, and then stirred at room temperature for 18 hours. Then additional thionyl chloride (0.1 ml) was added and the reaction mixture was heated to 40° C. for 4 more hours. After cooling, the solvent was removed in vacuo and the resulting golden brown, semi-solid product mixture was purified via flash chromatography (20 ml fractions, 2'×7' column, 1:9 ethyl acetate/hexanes) to yield a brown solid, m.p. of 57°–63° C.

EXAMPLE 7

N-(4'-chloro-3'-propargyloxyphenyl)-3-(trifluoromethyl)glutaramic acid (Compound 42)

Into a 200 ml 1-necked, round-bottomed flask were added 3-methylglutaric anhydride (0.35 g, 2.8 mmol), 4-chloro-3-(propargyloxy)aniline (0.50 g, 2.8 mmol), and 10 ml THF. The reaction mixture was stirred at room temperature for 18 hours then concentrated in vacuo to afford the desired product as a tan solid (0.86 g, quantitative yield), m.p. 128°–130° C.

Using the same procedure as used in this example, Compound 30 was prepared except that 2,4-dichloro-5-(propargyloxy)aniline was used in place of the 4-chloro-3-(propargyloxy)aniline.

EXAMPLE 8

N-(4'-chloro-2'-fluoro-5'-isopropyloxyphenyl)-5-hydroxy-3-(trifluoromethyl)pentanamide (Compound 45)

To a solution of N-(4'-chloro-2'-fluoro-5'-isopropyloxyphenyl)-3-(trifluoromethyl)glutaramic acid (4.32 g, 11.4 mmol) in 20 ml of tetrahydrofuran, (freshly distilled from sodium/benzophenone) was slowly added 10M borane-methyl sulfide complex (1.18 ml) via syringe. The temperature was maintained at 10°–20° C. with an ice bath while vigorous bubbling was evident. The mixture was allowed to warm slowly to room temperature and stirred 150 hrs while kept under nitrogen, heated to 55° C. for 6 hours, then cooled to room temperature and allowed to stand for 16 hours. The flask was cooled in an ice/water bath, then 7 ml of methanol (MeOH) were added slowly via addition funnel. The reaction mixture became too thick to continue stirring. It was allowed to warm slowly to room temperature, when the stir bar was again able to stir the mixture. The MeOH and THF were removed in vacuo (20–50 Torr) and the residue was flash chromatographed (2"×7" column, 3:1 hexanes/ethyl acetate, 75 ml fractions). Fractions 18–45 were combined and the solvent was removed in vacuo. The residue was dried in the vacuum oven at 50° C. to yield 1.66 g (39% yield) of the pentanamide as a nearly colorless oil.

EXAMPLE 9

N-(4-propargyl-2H-1,4-benzoxazin-3(4H)-one-6-yl)-3-(trifluoromethyl)glutaramic acid (Compound 70)

a. 6-nitro-2H-1,4-benzoxazin-3(4H)-one

To a mixture of 10.6 g (182 mmol) of potassium fluoride and 55 ml of anhydrous dimethylformamide was added 7.76 ml (72 mmol) of ethyl bromoacetate and the reaction mixture was stirred at room temperature for 15 minutes. Then 10.79 g (70.0 mmol) of 2-amino-4-nitrophenol was added and the reaction mixture was heated to 55° C. for 6 hours. The reaction mixture was cooled slowly to room temperature, stirred for 12 hours and poured onto 300 ml ice. The solid which formed was filtered off, washed with water and dried (20-50 Torr, 50° C., 16 hrs). The resulting orange solid was taken up in 100 ml EtOAc and 100 ml H$_2$O. The aqueous layer was extracted with EtOAc (2×100 ml). The organic layers were then combined and washed with water (3×150 ml) and 10% HCl and dried (MgSO$_4$). The solvent was removed in vacuo and the resulting solid was recrystallized from ethylene dichloride to yield 3.6 g (27% yield) of 6-nitro-2H-1,4-benzoxazin-3(4H)-one as an orange solid, m.p. 221°-223° C.

b. 6-nitro-4-propargyl-2H-1,4-benzioxazin-3(4H)-one

While kept under N$_2$, 0.81 g (20 mmol) of sodium hydride (60% dispersion in oil) was washed with 3 ml of pentanes and suspended in 20 ml of anhydrous dimethylformamide. While cooling with an ice/brine bath, 3.59 g (18.5 mmol) of 6-nitro-2H-1,4-benzoxazin-3(4H)-one was added through a dry powder funnel (exotherm of about 5° C.). An additional 10 ml of DMF was added and the mixture was stirred at 0° C. for 30 minutes. There was then added 2.06 ml (18.5 mmol) of an 80% solution of propargyl bromide in toluene and the mixture was stirred at room temperature for 12 hrs. The reaction mixture was poured into 50 ml of water and extracted with EtOAc (2×50 ml). The organic layers were combined, washed with water (2×50 ml) and dried (MgSO$_4$). The solvent was removed in vacuo to yield 6-nitro-4-propargyl-2H-1,4-benzoxazin-3(4H)-one as a yellow solid, 4 g (93% yield).

c. 6-amino-4-paragyl-2H-1,4-benzoxazin-3(4H)-one

To a slurry of 5.1 g (91 mmol) of iron powder in 42.5 ml of 5% aqueous acetic acid was added dropwise a solution of 4 g of 6-nitro-4-propargyl-2H-1,4-benzoxazin-3(4H)-one dissolved in 42.5 ml of glacial acetic acid and 42.5 ml of EtOAc. The reaction mixture was heated to gentle reflux for 1 hour then cooled to room temperature. The iron was removed by suction filtration. EtOAc (50 ml) was added to the filtrate and the layers were separated. The aqueous phase was extracted with EtOAc (2×50 ml) and the organic layers were combined, washed with saturated aqueous sodium bicarbonate solution (100 ml), and dried (MgSO$_4$). The solvent was removed in vacuo to yield a thin brown oil which was taken up in 50 ml of water and reextracted with EtOAc (3×50 ml). The organic layers were combined, washed with water (2×50 ml) and then dried (MgSO$_4$). The solvent was removed in vacuo to yield 2.55 g (75% yield) of 6-amino-4-propargyl-2H-1,4-benzoxazin-3(4H)-one as a dark brown solid, m.p. 136°-140° C.

The 6-amino-4-propargyl-2H-1,4-benzoxazin-3(4H)-one was reacted with 3-(trifluoromethyl)glutaric anhydride as described in Example 2 to yield the desired product, m.p. 158°-159° C.

Using the same procedure as used in this example, Compounds 69, 71 and 77 described in Tables III and IV were also prepared except methyl 2-chloropropionate was used in place of ethyl bromoacetate for Compound 69; phosgene in ethyl acetate was used to react with the 2-amino-4-nitrophenol for Compound 71; and 3-methylglutaric anhydride was used in place of 3-(trifluoromethyl)glutaric anhydride for Compound 77.

Using the same procedure as parts b and c of this example, Compound 114 was prepared starting with 6-nitroindole.

EXAMPLE 10

N-(4-allyl-7-fluoro-2H-1,4-benzoxazin-3(4H)-one-6-yl)-3-(trifluoromethyl)glutaramic acid (Compound 83).

a. Methyl 5-fluoro-2-nitrophenoxyacetate

To 100 g (0.64 mol) of 5-fluoro-2-nitrophenol in 1000 ml of methyl ethyl ketone were added 105 g (0.76 mol) K$_2$CO$_3$ (freshly ground) followed by 107 g (0.70 mol) of methyl bromoacetate. The reaction mixture was refluxed for 6 hours then cooled to room temperature and stirred for an additional 18 hours. The reaction mixture was poured into 1 L of water, the phases were separated, and the aqueous phase was extracted with EtOAc (2×600 ml). The combined organics were then dried (Na$_2$SO$_4$) and concentrated in vacuo to give 135 g (93% yield) of the desired product as a yellow solid, m.p. 85°-57° C.

b. Methyl 2,4-dinitro-5-fluorophenoxyacetate

To a solution of 14.5 g (63 mmol) methyl 5-fluoro-2-nitrophenoxyacetate in 17 ml conc. sulfuric acid (H$_2$SO$_4$) at 8° C. was added slowly via an addition funnel a mixture of 5.0 ml (76 mmol) of 70% nitric acid and 5.0 ml of conc. H$_2$SO$_4$. After addition was complete, the reaction was stirred an additional 1 hour at 15° C. The reaction mixture was poured into 150 ml of 1:1 ethyl acetate/water and the resulting layers were separated. The aqueous phase was extracted with ethyl acetate (2×60 ml) and the combined organics were dried (Na$_2$SO$_4$) and concentrated in vacuo to give 17.2 g (98% yield) of the desired nitrated product as a yellow solid.

c. 6-amino-7-fluoro-2H-1,4-benzoxazin-3(4H)-one

To a suspension of 12.2 g (0.22 mol) of iron powder in 100 ml of 5% aqueous acetic acid was added dropwise a solution of 10.0 g (36.5 mmol) of methyl 2,4-dinitro-5-fluorophenoxyacetate in 100 ml of EtOAc and 100 ml of glacial acetic acid. The reaction mixture was stirred at room temperature for 18 hours. The iron was removed by suction filtration through a small pad of Celite ® and the filter pad was rinsed with 50 ml of EtOAc. The filtrate was transferred to a separatory funnel and the phases were separated. The aqueous layer was extracted with EtOAc (3×50 ml) and the combined organic phases were washed with sodium bicarbonate (2×50 ml), dried over Na$_2$SO$_4$ and filtered. The solvent was removed from the filtrate in vacuo to yield 3.9 g (60% yield) of 6-amino-7-fluoro-2H-1,4-benzoxazin-3(4H)-one as a brown solid.

d. 4-allyl-6-amino-7-fluoro-2H-1,4-benzoxazin-3(4H)-one

While kept under N$_2$, 2.41 g (60.4 mmol) of sodium hydride (60% dispersion in oil) was washed with 10 ml hexanes and then suspended in 20 ml anhydrous dimethylformamide. A solution of 10.0 g (54.9 mmol) of 6-amino-7-fluoro-2H-1,4-benzoxazin-3(4H)-one in 100 ml of dimethyl formamide was added to the sodium hydride slurry slowly by syringe with ice cooling and the reaction mixture was stirred at room temperature for 0.5 hr. Then there was added 7.91 g (65.9 mmol) of allyl bromide by syringe with ice bath cooling. The reaction mixture was allowed to warm to room temperature, and then poured into 100 ml of water. The resulting mixture was extracted with EtOAc (2×50 ml) and the organic layers were combined and washed with water (3×50 ml), dried over $Na_2SO_4$ and filtered. The solvent was removed in vacuo to yield 11.0 g (90% yield) of 4-allyl-6-amino-7-fluoro-2H-1,4-benzoxazin-3(4H)-one as a brown solid.

The 4-allyl-6-amino-7-fluoro-2H-1,4-benzoxazin-3(4H)-one was reacted with 3-(trifluoromethyl)glutaric anhydride as described in Example 2 to obtain the desired product, m.p. 171°–172° C.

Using the same procedure as used in this example, Compounds 79, 91, 92, 106, 107, 120, 132, 137, 146, 149, 152 and 162 described in Table III were also prepared using the appropriately substituted alkyl halide or mesylate.

This procedure was also used to prepare Compound 78, except that 3-methylglutaric anhydride was used in place of 3-(trifluoromethyl)glutaric anhydride. Compound 154 was prepared using substantially the same procedure and substituting ethyl 2-bromobutyrate for methyl bromoacetate.

EXAMPLE 11

N-(4-propargyl-2H-1,4-benzthiazin-3(4H)-one-6-yl)-3-(trifluoromethyl)glutaramic acid (Compound 84)

a. ethyl S-(2,4-dinitrophenyl)mercaptoacetate

Into a 100 ml round-bottomed flask were placed 14.8 g (10 ml, 79.6 mmol) 2,4-dinitrofluorobenzene, THF (20 ml, freshly distilled from sodium benzophenone) and triethylamine (11.1 ml, 79.6 mmol). The reaction was cooled in an ice bath while 9.55 g (8.73 ml, 79.6 mmol) ethyl 2-mercaptoacetate dissolved in THF (10 ml) was added dropwise. The resulting nearly black solution was allowed to warm slowly to room temperature and stirred 18 hours. The reaction mixture was poured onto 150 ml ice and the resulting layers were separated. The aqueous phase was extracted with EtOAc (2×125 ml). The organic layers were combined and washed with water (100 ml), dried over $MgSO_4$ and concentrated to dryness in vacuo to yield 16.9 g of red-brown solid (74.1% yield).

b. 6-amino-2H-1,4-benzthiazin-3(4H)-one

To a suspension of iron powder (15 g, 0.27 mol) in 21.7 ml of 5% aqueous acetic acid was added dropwise via addition funnel, a solution of ethyl S-(2,4-dinitrophenyl)mercaptoacetate (5.91 g, 20.6 mmol) in 20.6 ml glacial acetic acid and 21 ml EtOAc. The reaction mixture was heated to 80° C. for 2 hours, then cooled to room temperature. The iron was removed by suction filtration and the filtrate was extracted with EtOAc (3×75 ml). The combined organic layers were washed once with 100 ml water and twice with 100 ml saturated aqueous sodium bicarbonate, dried ($MgSO_4$) and concentrated to dryness in vacuo to yield 2.3 g of a dark brown solid.

The 6-amino-2H-1,4-benzthiazin-3(4H)-one was alkylated with propargyl bromide as described in Example 9b, then converted to Compound 84 using the procedures described in Example 2.

Compound 122 was prepared using susbstantially the same procedure except theat 2,4-dinitro-1,5-difluorobenzene was used in place of 2,4-dinitrofluorobenzene.

EXAMPLE 12

N-(7-fluoro-4-isobutyl-2H-1,4-benzoxazin-3(4H)-one-6-yl)-3-(trifluoromethyl)glutaramic acid (Compound 87)

a. methyl 5-fluoro-2-nitrophenoxyacetate

To 10 g (63.7 mmol) of 5-fluoro-2-nitrophenol in 100 ml of methyl ethyl ketone was added 10.5 g (76.4 mmol) of finely ground potassium carbonate followed by 10.7 g (70.1 mmol) of methyl bromoacetate. The resulting suspension was refluxed for 6 hours and then stirred at room temperature overnight. During this time it went from a deep red color to pale yellow. The reaction was poured into one liter of water, the layers were separated and the aqueous layer was extracted twice more with EtOAc (2×100 ml). The organics were combined, dried ($Na_2SO_4$), filtered and evaporated to dryness in vacuo to give 13.3 g (91% yield) of methyl 5-fluoro-2-nitrophenoxyacetate as a light yellow solid (m.p. 85°–87° C.).

b. 7-fluoro-2H-1,4-benzoxazin-3(4H)-one

To 500 mg of 5% Pd/C in a Parr bottle was added 100 ml of EtOH followed by 5.0 g (21.8 mmol) of methyl 5-fluoro-2-nitrophenoxyacetate. The flask was placed in a Parr Apparatus, evacuated and then charged with hydrogen. The suspension was then shaken for 2 hours. After evacuating the flask and recharging with nitrogen, the solids were removed by vacuum filtration through Celite ®. Since some product does precipitate, the filter cake is repeatedly rinsed with EtOAc (200 ml). The filtrate is refluxed for 4 hours and then evaporated to dryness in vacuo to give the desired material, 7-fluoro-2H-1,4-benzoxazin-3(4H)-one, as a white solid (m.p. 201°–202° C.) in quantitative yield.

c. 7-fluoro-4-isobutyl-2H-1,4-benzoxazin-3(4H)-one

To 3.96 g (99 mmol) of hexanes washed 60% sodium hydride in 150 ml of N,N-dimethylformamide was added portionwise as a solid 15 g (90 mmol) of 7-fluoro-2H-1,4-benzoxazin-3(4H)-one. When the addition was complete the reaction was stirred at room temperature for 10 min, after which time 19.8 g (108 mmol) of isobutyl iodide was added. The reaction was then stirred overnight before quenching onto 200 ml of water. The aqueous phase was extracted with EtOAc (2×150 ml) and the combined organics were dried over $Na_2SO_4$, filtered and evaporated in vacuo to give the desired alkylated product, as a yellow oil (13 g, 65% yield).

d. 7-fluoro-4-isobutyl-6-nitro-1,4-benzoxazin-3(4H)-one

To 2.50 g (11.2 mmol) of 7-fluoro-4-isobutyl-2H-1,4-benzoxazin-3(4)-one in 25 ml of acetic anhydride was added dropwise over 10 min. a solution of 2.5 g (26.9 mmol) of 70% nitric acid in 5 ml of glacial acetic acid. After the addition was complete, the reaction was stirred for 1 hour at room temperature then it was quenched by pouring into 50 ml of ice/water. The resulting white precipitate was collected by vacuum filtration and dried in a vacuum oven at 60° C. overnight to yield 2.71 g (90% yield) of the desired nitrated product, m.p. 108°–110° C.

e. 6-amino-7-fluoro-4-isobutyl-1,4-benzoxazin-3(4H)-one

To 2.82 g (50.5 mmol) of iron powder suspended in 30 ml of 5% glacial acetic acid was added dropwise over 0.5 hour a solution of 2.71 g (10.1 mmol) of 7-fluoro-4- isobutyl-6-nitro-1,4-benzoxazin-3(4H)-one in 60 ml of 1:1 EtOAc/glacial acetic acid. After addition was complete, the reaction was refluxed for 2 hours then the solids were removed by vacuum filtration. The filtrate was extracted with EtOAc (2×100 ml) and the combined organic layers were washed with NaHCO$_3$ (sat'd, 2×150 ml) and dried over Na$_2$SO$_4$ before filtering and concentrating (in vacuo) to give 2.32 g (96% yield) of the desired aniline, 6-amino-7-fluoro-4-isobutyl-1,4-benzoxazin-3(4H)-one as a red semisolid.

The 6-amino-7-fluoro-4-isobutyl-1,4-benzoxazin-3(4H)-one was reacted with 3-(trifluoromethyl)glutaric anhydride as described in Example 2 to yield the desired product, m.p. 176°–178° C.

Using the appropriate alkylating agent in place of isobutyl iodide in step c, the above procedures were used to prepare Compounds 82, 86, 89, 90, 93, 97, 102, 108, 109, 125 and 131. Compound 147 was prepared following substantially these procedures and using the reaction conditions used in Example 21a in place of Example 12c.

Compound 157 was prepared using substantially the above procedures except propargyl bromide was used in place of isobutyl iodide and the resulting 6-amino-7-fluoro-4-propargyl-1,4-benzoxazin-3(4H)-one was reacted with 3-(difluoromethyl)glutaric anhydride as described in Example 2.

EXAMPLE 13

N-[5'-(3-butynyloxy)-4'-chloro-2'-fluorophenyl]-3-(trifluoromethyl)glutaramic acid (Compound 94)

Potassium carbonate (7.8 g, 56 mmol) was added to a solution of 5-amino-2-chloro-4-fluorophenol (3.23 g, 19.9 mmol) in 50 ml methyl ethyl ketone and the reaction mixture was stirred at room temperature for 1 hour. Then 4.2 g (19.9 mmol) 4-phenylsulfonyloxy-1-butyne (prepared from benzenesulfonyl chloride and 3-butyn-1-ol according to known procedure) was added and the reaction mixture was refluxed for 24 hours. The reaction was poured into 50 ml water and the layers were separated. The aqueous layer was extracted with EtOAc (1×50 ml) and the combined organics were washed with H$_2$O (3×50 ml), dried over MgSO$_4$, and concentrated. The residue was dissolved in 110 ml CH$_2$Cl$_2$ and filtered through a short pad of silica gel which was repeatedly rinsed with CH$_2$Cl$_2$ (4×100 ml). The combined organics were concentrated in vacuo to yield 0.95 g (22% yield) of the desired product as a brown oil.

The aniline was reacted with 3-(trifluoromethyl)glutaric anhydride as described in Example 2 to yield the desired product, m.p. 136°–137° C.

Using the same procedure as used in this example, compounds 95, 150, 151, 153 and 155 were prepared except the appropriate alkylating agent (prepared from methanesulfonyl chloride and an alcohol according to known procedures), for example, 2-methylsulfonyloxy-3-butyne, was used in place of 4-phenylsulfonyloxy-1-butyne.

EXAMPLE 14

N-(3-acetamido-4-methoxyphenyl)-3-(trifluoromethyl)-glutaramic acid (Compound 101)

2-Methoxy-5-nitroaniline was purchased and acetylated using HOAc/Ac$_2$O in H$_2$O/THF according to known procedures to made 2-methoxy-5-nitroacetanilide. This was reduced using catalytic hydrogenation (PtO$_2$, H$_2$, EtOH) to afford 3-acetamido-4-methoxyaniline which was reacted as described in Example 2 to yield the desired glutaramic acid.

EXAMPLE 15

N-(4-methoxymethyl-2H-1,4-benzoxazin-3(4H)-one-6-yl)-3-(trifluoromethyl)glutaramic acid (Compound 113)

a. 6-nitro-2H-1,4-benzoxazin-3(4H)-one

To a slurry of 2-amino-4-nitrophenol (10.7 g, 69.4 mmol) in 150 ml of CH$_2$Cl$_2$ was added 19.37 ml (139 mmol) of triethylamine and the mixture was stirred until homogenous. The reaction flask was then cooled to 0° C. while a solution of chloroacetyl chloride (11.06 ml, 139 mmol) in CH$_2$Cl$_2$ (50 ml) was added dropwise. The reaction was allowed to warm to room temperature and stirred for 16 hours after which time it was poured onto 250 ml of ice. The resulting white precipitate was coolected by vacuum filtration, washed with CH$_2$Cl$_2$ (25 ml) and dried in a vacuum oven at 50° C. to yield 20.56 g (90% yield) of the desired intermediate product.

To a solution of 7.82 g (25.6 mmol) of N,O-bis-(chloromethylcarbonyl)-2-amino-4-nitrophenol in 25 ml of THF was added 2.67 ml (51.2 mmol) of 50% NaOH and 10 ml of water. The two phase reaction mixture was stirred at room temperature for 16 hours then the solvents were removed in vacuo. The residue was partitioned between Et$_2$O (100 ml) and water (100 ml) and the layers were separated. The aqueous layer was extracted sequentially with Et$_2$O (2×100 ml) and EtOAc (2×100 ml) and the combined organic phases were dried over MgSO$_4$ and concentrated in vacuo to give 1.3 g (26% yield) of the desired product (m.p. 223°–228° C.) as a yellow solid.

b. 4-methoxymethyl-6-nitro-2H-1,4-benzoxazin-3(4H)-one

To 0.976 g (5.02 mmol) of 6-nitro-2H-1,4-benzoxazin-3(4H)-one in 100 ml of chloroform was added 2 ml of dimethoxymethane. Phosphorous pentoxide (5 g, 35 mmol) was added portionwise and the reaction mixture was stirred at room temperature for 16 hours. TLC analyses showed the starting material was still present therefore additional dimethoxymethane (2 ml) was added along with several batches of phosphorous pentoxide (2×1.2 g and 2.0 g) and chloroform (50 ml). The reaction was stirred for an additional 16 hours then cautiously quenched with water (50 ml). The reaction mixture was slowly neutralized with 50 ml of 1N NaOH during which time an exotherm occurred. When the reaction mixture had cooled to room temperature, the layers were separated and the aqueous phase was extracted with chloroform (2×50 ml). The combined organic phases were washed with water (2×50 ml), dried over MgSO$_4$ and concentrated to afford the desired product (0.5 g, 42% yield) as a pale yellow solid.

The nitro compound was reduced using the procedure described in Example 9c to yield 6-amino-4-methoxymethyl-2H-1,4-benzoxazin-3-one which was reacted with 3-(trifluoromethyl)glutaric anhydride as described in Example 2 to yield the desired product, m.p. 120°–122° C.

Using the procedure as described in this example except 9b was used in place of part b, Compounds 99, 105 and 141 were prepared using the appropriate alkylating agent.

EXAMPLE 16

N-(5'-amino-4'-chloro-2'-fluorophenyl)-3-(trifluoromethyl)glutaramic acid (Compound 144)

To 100 ml absolute ethanol in a Parr bottle was added 3.21 g (8.61 mmol) N-(4'-chloro-2'-fluoro-5'-nitrophenyl)-3-(trifluoromethyl)glutaramic acid (Compound 142). After bubbling nitrogen through the solution for 15 minutes, 100 mg platinum (IV) oxide was added. The flask was placed on a Parr apparatus and shaken for 1 hr under an atmosphere of hydrogen. The solids were removed by filtration through Celite and the filtrate was concentrated to dryness to give 3.1 g (100% yield) of an off-white solid containing N-(5'-amino-4'-chloro-2'-fluorophenyl)-3-(trifluoromethyl)glutaramic acid, m.p. 140°–142° C.

EXAMPLE 17

N-[4'-chloro-2'-fluoro-5'-(4",4"-dimethyl-2-oxazolin-2-yl)phenyl]-3-(trifluoromethyl)glutaramic acid (Compound 148)

a. 2-chloro-4-fluoro-5-nitrobenzoyl chloride

To a solution of 2-chloro-4-fluoro-5-nitrobenzoic acid (4.0 g, 18 mmol) in 65 ml toluene was added 2 drops of DMF followed by 1.8 ml (25 mmol) thionyl chloride. The mixture was heated to reflux for 18 hr, cooled to ambient temperature and the solvent was removed in vacuo to afford 4.0 g (93% yield) of a white solid identified by IR and NMR as the desired benzoyl chloride. The crude material was used directly in the following procedure.

b. N-(1,1-dimethyl-2-hydroxyethyl)-2-chloro-4-fluoro-5-nitrobenzamide

To a cooled (0° C.) solution of 2-amino-2-methyl-1-propanol (2.4 ml, 2.2 g, 25 mmol) in $CH_2Cl_2$ (10 ml), was added dropwise via an addition funnel 3.0 g (12 mmol) 2-chloro-4-fluoro-5-nitrobenzoyl chloride in 20 ml $CH_2Cl_2$. Following the addition, the mixture was allowed to warm to room temperature and a white precipitate formed. After 1.5 hr, 10 ml water was added and the mixture was filtered to afford 2.1 g of a pale yellow solid identified by NMR to be the desired product. The filtrate was extracted with EtOAc (3×75 ml) and the combined organic phases were washed with brine, saturated sodium bicarbonate, and again with brine then dried over $MgSO_4$. Concentration gave 1.0 g of additional product (3.1 g, 86% total yield).

c. 2-(2'-chloro-4'-fluoro-5'-nitrophenyl)-4,4-dimethyl-2-oxazoline

To a suspension of N-(1,1-dimethyl-2-hydroxyethyl)-2-chloro-4-fluoro-5-nitrobenzamide (2.0 g, 6.9 mmol) in 30 ml EtOAc was added dropwise 1.6 ml (2.6 g, 2.2 mmol) thionyl chloride. The resulting clear, yellow solution was stirred at room temperature for 25 minutes during which time a white precipitate formed. The reaction was then treated with 30 ml 10% NaOH causing a slight exotherm as the solids dissolved. The aqueous phase was extracted with EtOAc (3×25 ml) and the combined organics were washed with brine and dried ($MgSO_4$). Concentration afforded 1.85 g (98% yield) of product as a yellow solid.

The 2-(2'-chloro-4'-fluoro-5'-nitrophenyl)-4,4-dimethyl-2-oxazoline was reduced as described in Example 9c to the corresponding aniline which was converted to the glutaramic acid (Compound 148) using the procedure of Example 2.

EXAMPLE 18

N-(6-fluoro-3-propyl-2H-1,3-benzoxazin-2(3H)-one-5-yl)-3-(trifluoromethyl)glutaramic acid (Compound 118)

a. 2-amino-5-fluorophenol

To 500 mg of 10% palladium on carbon in a Parr bottle with 50 ml of anhydrous ethanol was added a solution of 10 g (64 mmol) 5-fluoro-2-nitrophenol in 150 ml ethanol. The flask was evacuated, charged with hydrogen and shaken on a Parr apparatus for 1 hour. The catalyst was removed by filtration through Celite ® and the filtrate was evaporated to dryness in vacuo to give 7.54 g (93% yield) of a dark solid shown to be the desired product by $^1H$ NMR.

b. 6-fluoro-1,3-benzoxazolin-2(3H)-one

To 5.0 g (39.3 mmol) 2-amino-5-fluorophenol in 150 ml of $CH_2Cl_2$ at 0° C. was added 13.4 (98 mmol) of potassium carbonate and 23 g (47 mmol) of 20 wt % phosgene in toluene. After warming to room temperature, the reaction was stirred an additional hour before pouring into 200 ml ice/water. The layers were separated and the aqueous phase was extracted with EtOAc (1×100 ml) before the organics were combined and dried over $Na_2SO_4$. The solvent was removed in vacuo to give 5.76 g (96% yield) of the desired product as determined by $^1H$ NMR.

c. 6-fluoro-3-n-propyl-1,3-benzoxazolin-2(3H)-one

To 670 mg (16.74 mmol) of hexanes washed sodium hydride in 20 ml DMF was added a solution of 2.33 g (15.22 mmol) 6-fluoro-1,3-benzoxazolin-2(3H)-one in 40 ml DMF. The reaction was stirred for 10 minutes before 3.11 g (18.3 mmol) 1-iodopropane was added and then stirred for 3 hr at room temperature. After pouring into 50 ml of ice/water, the aqueous phase was extracted with EtOAc (2×100 ml). The combined organic layers were washed with water (1×100 ml), dried over $Na_2SO_4$ and evaporated to dryness in vacuo to give 2.2 g (75% yield) of the alkylated product as a brown solid.

d. 6-fluoro-5-nitro-3-n-propyl-1,3-benzoxazolin-2(3H)-one

To 2.0 g (10.3 mmol) 6-fluoro-3-n-propyl-1,3-benzoxazolin-2(3H)-one in 25 ml acetic anhydride was added dropwise a solution of 2.3 g (24.7 mmol) 70% nitric acid in 2 ml glacial acetic acid. After addition was completed, the reaction was stirred at room temperature for 2 hours then poured into 50 ml ice/water. The aqueous phase was extracted with EtOAc (2×70 ml) and the combined organics were dried over $Na_2SO_4$ and evaporated to dryness in vacuo to give 1.66 g (67% yield) of the nitrated product as a yellow oil.

The 6-fluoro-5-nitro-3-n-propyl-1,3-benzoxazolin-2(3H)-one prepared above was reduced to the corresponding aniline following the procedure of Example 12e and the aniline was reacted with 3-(trifluoromethyl)glutaric anhydride as described in Example 2 to yield the desired product, m.p. 173°–176° C.

EXAMPLE 19

N-(6-fluoro-1-n-propyl-4H-1,3-benzoxazin-2(1H)-one-7-yl)-3-(trifluoromethyl)glutaramic acid (Compound 129)

a. 3,1,4-benzoxazin-2(1H)-one

To 4.0 g (32.5 mmol) 2-aminobenzyl alcohol in 200 ml $CH_2Cl_2$ at 0° C. was added 11.12 g (81.2 mmol) potassium carbonate followed by 19.3 g (39.0 mmol) 20 wt % phosgene in toluene. The reaction was slowly warmed to room temperature and then stirred for 5 hours. The reaction mixture was poured into 200 ml saturated NaHCO$_3$, the layers were separated and the organic phase was dried over Na$_2$SO$_4$. Concentration gave 4.55 g (84% yield) of the desired product as a white solid.

This 3,1,4-benzoxazin-2(1H)-one was converted to the desired glutaramic acid (m.p. 160°-161° C.) as described in Examples 12 c-e and Example 2 except that 1-iodopropane was used in place of isobutyl iodide.

EXAMPLE 20

N-(4-allyl-7-fluoro-2H-1,4-benzoxazin-3(4H)-one-6-yl)-3-(trifluoromethyl)glutaramic acid, ammonium salt (Compound 116)

To 550 mg (1.36 mmol) N-(4-allyl-7-fluoro-2H-1,4-benzoxazin-3(4H)-one-6-yl)-3-(trifluoromethyl)-glutaramic acid (Compound 83) in 20 ml acetone was added 2 ml aqueous ammonia. The reaction mixture was stirred at room temperature for 0.5 hour before the solvent was removed in vacuo to give 570 mg (100% yield) of the desired ammonium salt as a white solid, m.p. 150°-153° C.

Compound 117 was prepared using the above procedure except 1 equivalent of potassium hydroxide was used in place of ammonia.

EXAMPLE 21

N-(4'-chloro-2'-fluoro-5'-(methoxymethoxy)phenyl)-3-(trifluoromethyl)glutaramic acid (Compound 115)

a. 4-chloro-2-fluoro-5-(methoxymethoxy)nitrobenzene

To 1.12 g (5.9 mmol) of 2-chloro-4-fluoro-5-nitrophenol in 100 ml CH$_2$Cl$_2$ was added 2 ml of dimethoxymethane followed by 7.48 g (53 mmol) of phosphorus pentoxide. The reaction was stirred at room temperature for 3 hours after which time an additional 100 ml of CH$_2$Cl$_2$ was added. The reaction was poured onto 200 ml ice and the resulting layers were separated. The aqueous phase was extracted once more with water (2×100 ml), dried over MgSO$_4$ and concentrated to afford 1.16 g (95% yield) of the desired product as a pale yellow solid.

The nitrobenzene intermediate was converted to the corresponding aniline using iron and acetic acid as described in Example 12e. This aniline was reacted with 3-(trifluoromethyl)glutaric anhydride as described in Example 2 to prepare Compound 115, m.p. 78°-80° C.

EXAMPLE 22

N-(4'-chloro-2'-fluoro-5'-nitrophenyl)-3-(trifluoromethyl)glutaramic acid (Compound 142)

a. 4-chloro-2-fluoro-5-nitroacetanilide

Into a 500 ml, 3-necked round-bottomed flask equipped with a mechanical stirrer was placed 4-chloro-2-fluoroacetanilide (56.3 g, 0.3 mmol) and conc. H$_2$SO$_4$ (100 ml). While cooling to 0° C., fuming nitric acid (21 g, 0.33 mol) was added over 30 minutes then the reaction mixture was poured onto 2 liters of ice. When the ice had melted the solid product was collected by filtration, washed with water and dried in vacuo to give 44 g (63% yield) of the nitrated material as a tan solid.

b. 4-chloro-2-fluoro-5-nitroaniline

A mixture of 4-chloro-2-fluoro-5-nitroacetanilide (10.88 g, 46.8 mmol), 50.4 ml ethanol, 65.7 ml water, and 43.8 ml (526 mmol) concentrated hydrochloric acid was refluxed for one hour and then poured onto 300 ml ice. The aqueous phase was made strongly basic by the addition of 50% aqueous sodium hydroxide and was extracted with 2×200 ml Et$_2$O. The combined organic layers were washed with water (200 ml) and brine (200 ml), dried over Na$_2$SO$_4$ and concentrated to dryness in vacuo to give 8 g (90% yield) of the desired aniline as a yellow solid.

This aniline was reacted with 3-(trifluoromethyl)glutaric anhydride as described in Example 2 to yield the desired glutarimide, m.p. 120°-122° C.

EXAMPLE 23

N-[4'-chloro-5'-(3,3-dichloroallyloxy)-2'-fluorophenyl]-3-(trifluoromethyl)glutaramic acid (Compound 160)

Potassium hydroxide (1.95 g, 34.8 mmol) dissolved in 5 ml water was added to a solution of 5-amino-2-chloro-4-fluorophenol (5.65 g, 34.8 mmol) in 40 ml dimethylsulfoxide. The resulting mixture was stirred at room temperature for 18 hours, then poured into 100 ml water and extracted with Et$_2$O (2×100 ml). The combined organic layers were washed with water (2×100 ml), dried over Na$_2$SO$_4$, and filtered through a short pad of neutral alumina with Et$_2$O (3×50 ml rinses). The filtrate was concentrated in vacuo to yield 7.56 g (74% yield) of a brown oil containing mostly the desired product as identified by $^1$H NMR.

This crude aniline was reacted with 3-(trifluoromethyl)glutaric anhydride as described in Example 2 to yield the desired product, m.p. 117°-118.5° C.

Compound 159 was also prepared using this procedure only propargyl bromide was the alkylating agent and the aniline was reacted with 3-(difluoromethyl)glutaric anhydride instead of 3-(trifluoromethyl)glutaric anhydride.

EXAMPLE 24

N-(5'-isobutylsulfoxy-4'-chloro-2'-fluorophenyl)-3-(trifluoromethyl)glutaramic acid (Compound 163)

a. 4-chloro-2-fluoro-5-(isobutylthio)acetanilide

Potassium carbonate (26 g, 188 mmol) was added to a solution of 5-acetamido-2-chloro-4-fluorothiophenol (11.35 g, 52.4 mmol) in 50 ml anhydrous DMF and the reaction mixture was stirred at room temperature for 10 minutes. Then 6.63 ml (57.0 mmol) 1-iodo-2-methylpropane was added and the reaction was heated to 50° C. for 18 hours. The reaction was poured into 200 ml water, then suction filtered to isolate a nearly white solid which was dried in vacuo to yield 13.31 g (93% yield) of the alkylated product as an off-white solid.

b. 4-chloro-2-fluoro-5-(isobutylsulfoxy)acetanilide

To a solution of 4-chloro-2-fluoro-5-(isobutylthio)acetanilide (see Example 28a) (1.04 g, 3.8 mmol) in 30 ml ethanol, cooled to 0° C., was added sodium periodate (1.29 g, 6.0 mmol) in 6 ml water. The reaction was allowed to warm to room temperature and was stirred for 18 hours. The solids were removed by suction filtration and the filtrate was dissolved in 75 ml CH$_2$Cl$_2$ and then washed with water (50 ml). The organic layer was dried over Na$_2$SO$_4$ and concentrated to dryness to yield 1 g (90% yield) of the desired sulfoxide as a white solid.

c. 4-chloro-2-fluoro-5-(isobutylsulfonyl)aniline

Concentrated hydrochloric acid (16.65 ml, 200 mmol) was added to a slurry of 4-chloro-2-fluoro-5-(isobutylsulfoxy)acetanilide (5.46 g, 17.7 mmol) in water (24.85 ml) and ethanol (19.08 ml). The reaction mixture was refluxed for 2 hours, then poured onto 200 ml ice and made strongly basic by the addition of 50% NaOH. The aqueous phase was extracted with Et$_2$O (2×100 ml) and the combined organic layers were washed with water (1×100 ml) and brine (1×100 ml) then dried (Na$_2$SO$_4$) and concentrated in vacuo. The brown solid obtained (3.8 g, 81% yield) was shown by NMR to contain the desired aniline as the main component.

The 4-chloro-2-fluoro-5-(isobutylsulfonyl)aniline from above was reacted with 3-(trifluoromethyl)glutaric anhydride as described in Example 2 to prepare Compound 163, m.p. 110°–115° C.

The compounds of the present invention are broad spectrum herbicides and may be advantageously employed to control selectively monocot and/or dicot weeds in agronomic and horticultural crops, forestry, orchards, turf, vines or for total weed control.

The compounds of the present invention are useful both as preemergence and as postemergence herbicides. Preemergence herbicides may be applied to the soil surface or incorporated into the soil. Postemergence herbicides are those which are applied after the plants have emerged and during their growth period.

The compounds of the present invention are selective or non-selective, depending on the rate applied, the combination of plants to which they are applied and whether they are applied pre- or postemergent. Such variables are understood by those skilled in the art. At higher dosage rates they tend to be non-selective, while at lower dosage rates they tend to be selective. For example, the compounds of this invention have shown selectivity preemergence and/or postemergence in crops such as, but not limited to, wheat, corn, rice, soybeans, sunflower, peanuts and cotton.

The present glutaramic acids and derivatives may be applied in any amount which will give the required control of weeds. A preferred rate of application of the herbicides of the invention is from about 0.001 to about 12 pounds per acre and especially preferred from about 0.01 to about 5 pounds of the glutaramic acid or derivative compound per acre. Most preferably, a rate from about 0.02 to about 2 pounds per acre is used.

The glutaramic acids and derivatives of the present invention may be applied to the soil surface prior to plant emergence or incorporated into the soil or other growth medium prior to planting. This incorporation can be carried out by any convenient means, including by simply mixing with the soil, by applying the glutaramic acid or derivative to the surface of the soil and then disking or dragging into the soil to the desired depth, or by employing a liquid carrier to accomplish the necessary penetration and impregnation.

A glutaramic acid or derivative of the present invention can be applied postemergence to plants to be treated or to the growth medium either by itself, or, as is generally done, as a component in a herbicidal composition or formulation which also comprises an agronomically acceptable carrier. The concentration of the glutaramic acid in the herbicidal composition can vary from about 1% to about 98%.

By agronomically acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the glutaramic acids and derivatives of the present invention may also be used in any of these herbicidal formulations. The herbicidal compositions of the invention can be either solid or liquid formulations or solutions. For example, the glutaramic acids and derivatives can be formulated as wettable powders, solutions, emulsifiable concentrates, dusts, granular formulations, aerosols, water dispersable granular formulations or flowable concentrates as is known to one skilled in the art. In such formulations, the compounds are extended with a liquid or solid carrier and, when desired, suitable surfactants are incorporated. Examples of solvents which are useful in the practice of this invention include alcohols, ketones, aromatic hydrocarbons, halogenated hydrocarbons, dimethylformamide, dioxane, dimethyl sulfoxide, and the like.

It is usually desirable, particularly in post-emergence applications, to include adjuvants such as wetting agents, spreading agents, dispersing agents, sticking agents, adhesives, and the like, in accordance with agrigultural practices. Examples of adjuvants which are commonly used in the art can be found in the John W. McCutcheon, Inc. publication "Detergents and Emulsifiers Annual."

The glutaramic acids and derivatives of the present invention can also be mixed with fertilizers or fertilizing materials before their application. In one type of solid fertilizing composition in which the glutaramic acids and derivatives may be used, particles of a fertilizer or fertilizing ingredients, such as ammonium sulfate, ammonium nitrate, or ammonium phosphate can be coated with one or more of the glutaramic acids and derivatives. The solid glutaramic acid or derivative and solid fertilizing material may also be admixed in blending or mixing equipment, or they can be incorporated with fertilizers in granular formulations. Any relative proportion of glutaramic acid or derivative and fertilizer can be used which is suitable for the crops and weeds to be treated.

The glutaramic acids and derivatives of the present invention may be applied to herbicidal sprays by methods commonly employed, such as conventional high-gallonage hydraulic sprays, low gallonage sprays, air blast spray, aerial sprays and dusts.

For some applications, one or more other herbicides may be added to the glutaramic acids and derivatives of the present invention, thereby providing additional advantages and effectiveness. When mixtures of herbicides are employed, the relative proportions which are used will depend upon relative efficacy of the compounds in the mixture with respect to the plants to be treated. Examples of other herbicides which can be combined with the glutaramic acids and derivatives of the present invention include:

Carboxylic Acids and Derivatives 2,3,6-trichlorobenzoic acid and its salts;
2,3,5,6-tetrachlorobenzoic acid and its salts;
2-methoxy-3,5,6-trichlorobenzoic acid and its salts;
2-methoxy-3,6-dichlorobenzoic acid and its salts;
2-methyl-3,6-dichlorobenzoic acid and its salts;
2,3-dichloro-6-methylbenzoic acid and its salts;
2,4-dichlorophenoxyacetic acid and its salts and esters;
2,4,5-trichlorophenoxyacetic acid and its salts and esters;
2-methyl-4-chlorophenoxyacetic acid and its salts and esters;
2-(2,4,5-trichlorophenoxy)propionic acid and its salts and esters;
4-(2,4-dichlorophenoxy)butyric acid and its salts and esters;
4-(2-methyl-4-chlorophenoxy)butyric acid and its salts and esters;

2,3,6-trichlorophenylacetic acid and its salts;
3,6-endoxohexahydrophthalic acid and its salts;
dimethyl 2,3,5,6-tetrachloroterephthalate;
trichloroacetic acid and its salts;
2,2-dichloropropionic acid and its salts;
2,3-dichloroisobutyric acid and its salts;
isopropylammonium 2-(4-isopropyl-4-methyl-5-oxo-2-imidazolin-2-yl)nicotinate;
2-[4,5-dihydro-4-methyl-4-(1-methylethyl)-5-oxo-1H-imidazol-2-yl]-3-quinolinecarboxylic acid;
m-toluic acid, 6-(4-isopropyl-4-methyl-5-oxo-2-imidazolin-2-yl)-, methyl ester and p-toluic acid, 6-(4-isopropyl-4-methyl-5-oxo-2-imidazolin-2-yl)-, methyl ester;
N-(phosphonomethyl)glycine, isopropylammonium salt;
[3,5,6-trichloro-(2-pyridinyl)oxy]acetic acid;
3,7-dichloro-8-quinolinecarboxylic acid;
ammonium dl-homoalanin-4-yl(methyl)phosphinate;

Carbamic Acid Derivatives ethyl N,N-di(n-propyl)thiolcarbamate;
n-propyl N,N-di(n-propyl)thiolcarbamate;
ethyl N-ethyl-N-(n-butyl)thiolcarbamate;
n-propyl N-ethyl-N-(n-butyl)thiolcarbamate;
2-chloroallyl N,N-diethyldithiocarbamate;
N-methyldithiocarbamic acid salts;
ethyl 1-hexamethyleneiminecarbothiolate;
isopropyl N-phenylcarbamate;
isopropyl N-(m-chlorophenyl)carbamate;
4-chloro-2-butynyl-N-(m-chlorophenyl)carbamate;
methyl N-(3,4-dichlorophenyl)carbamate;
dinitro-o-(sec-butyl)phenol and its salts;
pentachlorophenol and its salts;
S-(4-chlorobenzyl)-N,N-diethylthiolcarbamate;

Substituted Ureas 2-chloro-N-[(4-methoxy-6-methyl-1,3,5-triazin-2-yl)aminocarbonyl]benzenesulfonamide;
3-(3,4-dichlorophenyl)-1,1-dimethylurea;
3-phenyl-1,1-dimethylurea;
3-(3,4-dichlorophenyl)-3-methoxy-1,1-dimethylurea;
3-(4-chlorophenyl)-3-methoxy-1,1-dimethylurea;
3-(3,4-dichlorophenyl)-1-n-butyl-1-methylurea;
3-(3,4-dichlorophenyl)-1-methoxy-1-methylurea;
3-(4-chlorophenyl)-1-methoxy-1-methylurea;
3-(3,4-dichlorophenyl)-1,1,3-trimethylurea;
3-(3,4-dichlorophenyl)diethylurea;
dichloral urea;
methyl 2-[[[[(4,6-dimethyl-2-pyrimidinyl)amino]carbonyl]amino]sulfonyl]benzoate;
N-((6-methoxy-4-methyl-1,3,5-triazin-2-yl)aminocarbonyl)-2-(2-chloroethoxy)benzenesulfonamide;
2-[[[(4-chloro-6-methoxypyrimidine-2-yl)aminocarbonyl]amino]sulfonyl]benzoic acid, ethyl ester;
methyl 2-[[[[(4-methoxy-6-methyl-1,3,5-triazin-2-yl)amino]carbonyl]amino]sulfonyl]benzoate;
methyl 3-[[[[(4-methoxy-6-methyl-1,3,5-triazin-2-yl)amino]carbonyl]amino]sulfonyl]-2-thiophenecarboxylate;
methyl 2-[[[[[(4,6-dimethoxypyrimidin-2-yl)amino]carbonyl]amino]sulfonyl]methyl]benzoate;
methyl 2-[[[[(4-methoxy-6-methyl-1,3,5-triazin-2-yl)methylamino]carbonyl]amino]sulfonyl]benzoate;

Substituted Triazines 2-chloro-4,6-bis(ethylamino)-s-triazine;
2-chloro-4-ethylamino-6-isopropylamino-s-triazine;
2-chloro-4,6-bis(methoxy-n-propylamino)-s-triazine;
2-methoxy-4,6-bis(isopropylamino)-s-triazine;
2-chloro-4-ethylamino-6-(3-methoxy-n-propylamino)-s-triazine;
2-methylmercapto-4,6-bis(isopropylamino)-s-triazine;
2-methylmercapto-4,6-bis(ethylamino)-s-triazine;
2-methylmercapto-4-ethylamino-6-isopropylamino-s-triazine;
2-chloro-4,6-bis(isopropylamino)-s-triazine;
2-methoxy-4,6-bis(ethylamino)-s-triazine;
2-methoxy-4-ethylamino-6-isopropylamino-s-triazine;
2-methylmercapto-4-(2-methoxyethylamino)-6-isopropylamino-s-triazine;
4-amino-6-(t-butyl)-3-(methylthio)-1,2,4-triazine-5(4H)-one;

Diphenyl Ether Derivatives 2,4-dichloro-4'-nitrodiphenyl ether;
2,4,6-trichloro-4'-nitrodiphenyl ether;
2,4-dichloro-6-fluoro-4'-nitrodiphenyl ether;
3-methyl-4'-nitrodiphenyl ether;
3,5-dimethyl-4'-nitrodiphenyl ether;
2,4'-dinitro-4-(trifluoromethyl)diphenyl ether;
2,4-dichloro-3'-methoxy-4'-nitrodiphenyl ether;
sodium 5-(2-chloro-4-(trifluoromethyl)phenoxy)-2-nitrobenzoate;
2-chloro-1-(3-ethoxy-4-nitrophenoxy)-4-(trifluoromethyl)benzene;
1-(carboethoxy)ethyl 5-[2-chloro-4-(trifluoromethyl)phenoxy]-2-nitrobenzoate;
5-[2-chloro-4-(trifluoromethyl)phenoxy]-N-(methylsulphonyl)-2-nitrobenzamide;

Anilides 2-chloro-N-(2-ethyl-6-methylphenyl)-N-(2-methoxy-1-methylethyl)acetamide;
2-chloro-2',6'-diethyl-N-(2-propyloxyethyl)acetanilide;
N-(3,4-dichlorophenyl)propionamide;
N-(3,4-dichlorophenyl)methacrylamide;
N-(3-chloro-4-methylphenyl)-2-methylpentanamide;
N-(3,4-dichlorophenyl)trimethylacetamide;
N-(3,4-dichlorophenyl)-alpha,alpha-dimethylvaleramide;
N-isopropyl-N-phenylchloroacetamide;
N-n-butoxymethyl-N-(2,6-diethylphenyl)chloroacetamide;
N-methoxymethyl-N-(2,6-diethylphenyl)chloroacetamide;

Oxyphenoxy Herbicides 2-(4-(2,4-dichlorophenoxy)phenoxy)methyl propionate;
methyl 2-(4-(3-chloro-5-(trifluoromethyl)-2-pyridinyloxy)phenoxy)propanoate;
butyl (R)-2-[4-[5-(trifluoromethyl)-2-pyridinyloxy]phenoxy]propionate;
ethyl 2-[4-[(6-chloro-2-benzoxazolyl)oxy]phenoxy]propanoate;
butyl 2-[4-[[5-(trifluoromethyl)-2-pyridinyl]oxy]phenoxy]propionate;
2-[4-[(6-chloro-2-quinoxalinyl)oxy]phenoxy]propionic acid, ethyl ester;

Uracils 5-bromo-3-s-butyl-6-methyluracil;
5-bromo-3-cyclohexyl-1,6-dimethyluracil;
3-cyclohexyl-5,6-trimethyleneuracil;
5-bromo-3-isopropyl-6-methyluracil;
3-tert-butyl-5-chloro-6-methyluracil;

Nitriles 2,6-dichlorobenzonitrile; diphenylacetonitrile;
3,5-dibromo-4-hydroxybenzonitrile;
3,5-diiodo-4-hydroxybenzonitrile;

Other Organic Herbicides 2-chloro-N,N-diallylacetamide;
N-(1,1-dimethyl-2-propynyl)-3,5-dichlorobenzamide;
maleic hydrazide;
3-amino-1,2,4-triazole;
monosodium methanearsonate;
disodium methanearsonate;
N,N-dimethyl-alpha,alpha-diphenylacetamide;
N,N-di(n-propyl)-2,6-dinitro-4-(trifluoromethyl)aniline;
N,N-di(n-propyl)-2,6-dinitro-4-methylaniline;
N,N-di(n-propyl)-2,6-dinitro-4-methylsulfonylaniline;
O-(2,4-dichlorophenyl)-O-methyl isopropylphosphoramidothioate;
4-amino-3,5,6-trichloropicolinic acid;
2,3-dichloro-1,4-naphthoquinone;
di(methoxythiocarbonyl)disulfide;
3-(1-methylethyl)-1H-2,1,3-benzothiadiazin-(4)3H-one-2,2-dioxide;
6,7-dihydrodipyridol[1,2-a:2',1'-c]pyrazidiium salts;
1,1'-dimethyl-4,4'-bipyridinium salts;
3,4,5,6-tetrahydro-3,5-dimethyl-2-thio-2H-1,3,5-thiadiazine;
2-[1-(ethoxyimino)butyl]-5-[2-(ethylthio)propyl]-3-hydroxy-2-cyclohexen-1-one;
2-(2-chlorophenyl)methyl-4,4-dimethyl-3-isoxazolidinone;
N-(1-ethylpropyl)-3,4-dimethyl-2,6-dinitrobenzamide;
4-chloro-5-(methylamino)-2-($\alpha,\alpha,\alpha$-trifluoro-m-toluyl)-3(2H)-pyridazinone;
2-(3,5-dichlorophenyl)-2-(2,2,2-trichloromethyl)oxirane.

The herbicidal activity of glutaramic acids and derivatives of the present invention towards a number of common weeds was evaluated using a greenhouse method of testing. Using the procedures described below, the glutaramic acids and derivatives of the present invention were evaluated for control of the following weeds:

| Monocots | |
|---|---|
| Barnyardgrass (BYG) | *Echinochloa crus-galli* |
| Crabgrass (CRB) | *Digitaria sanguinilis* |
| Foxtail (FOX) | *Setaria viridis* |
| Johnsongrass (JON) | *Sorghum halepense* |
| Meadow Foxtail (MF) | *Alopecurus pratensis* |
| Nutsedge (NUT) | *Cyperus esculentus* |
| Wild Oat (WO) | *Avena fatua* |
| Dicots | |
| Beggartick (BID) | *Bidens pilosa* |
| Cocklebur (CKL) | *Xanthium strumarium* |
| Morningglory (MG) | *Ipomoea lacunosa* |
| Nightshade (NS) | *Solanum nigrum* |
| Pigweed (PIG) | *Amaranthus retroflexus* |
| Smartweed (SMT) | *Polygonum lapathifolium* |
| Velvetleaf (VEL) | *Abutilon theophrasti* |

The following test procedure was employed. Seeds of selected plants were planted in flats or pots. For preemergence tests, immediately after planting, the test compound was sprayed directly onto the soil surface. The flats or pots were then watered by overhead irrigation. For postemergence tests, the seeds were allowed to germinate and grow for 10 to 21 days. Each series of test plants were selected for uniformity, size, and stage of developement. The test plants were then treated with the test compound. The plants for postemergence tests were watered by subirrigation only.

The compound to be evaluated was dissolved in an appropriate solvent, usually acetone, and sprayed over the flats or pots using a carrier volume equivalent to 25 to 50 gallons per acre at the rate of application in pounds per acre (lb./A) specified in the table. About ten to twenty-one days after application of the test compound, the state of growth of the plant was observed. Each species was evaluated on a scale of 0–100 in which 0 equals no activity and 100 equals total control. The following tables (Table VI and VII) show the results obtained for the test compounds at the stated rate of application.

TABLE VI

| | | | HERBICIDAL ACTIVITY | | | | | | | | |
|---|---|---|---|---|---|---|---|---|---|---|---|
| Compound No. | Rate (lb/A) | Type | CKL | MG | PIG | SMT | VEL | BYG | FOX | JON | NUT | WO |
| 1. | 1 | PRE | 0 | 0 | 0 | 0 | 0 | 0 | 0 | 0 | 0 | 0 |
|  | 1 | POST | 5 | 0 | 40 | 0 | 0 | 0 | 0 | 0 | 0 | 0 |
| 2. | 2 | PRE | 100 | 100 | 100 | — | 100 | 100 | 100 | 99 | 100 | 45 |
|  | 2 | POST | 100 | 100 | 100 | 100 | 100 | 100 | 100 | 10 | 100 | 30 |
| 3. | 2 | PRE | 0 | 100 | 100 | — | 100 | 100 | 100 | 95 | 100 | 70 |
|  | 2 | POST | 100 | 100 | 100 | 100 | 100 | 75 | 25 | 5 | 75 | 35 |
| 4. | 2 | PRE | 0 | 100 | 100 | 100 | 100 | 100 | 100 | 100 | 25 | 45 |
|  | 2 | POST | 85 | 100 | 100 | 100 | 95 | 85 | 15 | 5 | 0 | 0 |
| 5. | 2 | PRE | — | 35 | 100 | 100 | 100 | 60 | 98 | 35 | 20 | 0 |
|  | 2 | POST | 100 | 90 | 100 | 100 | 45 | 25 | 90 | 10 | 0 | 0 |
| 6. | 4 | PRE | 100 | 100 | — | 100 | 100 | 100 | 100 | 98 | 95 | 98 |
|  | 4 | POST | 100 | 100 | 100 | 100 | 100 | 100 | 80 | 35 | 15 | 55 |
| 7. | 1 | PRE | 0 | 60 | 100 | 100 | 100 | 70 | 95 | 100 | 0 | 0 |
|  | 1 | POST | 80 | 90 | 100 | 35 | 90 | 10 | 15 | 10 | — | 0 |
| 8. | 1 | PRE | 61 | 100 | 100 | 100 | 100 | 90 | 100 | 100 | 20 | 75 |
|  | 1 | POST | 50 | 100 | 100 | 100 | 100 | 25 | 100 | 100 | 0 | 20 |
| 9. | 2 | PRE | — | 100 | 100 | 100 | 100 | 100 | 100 | 100 | 35 | 60 |
|  | 2 | POST | 100 | 100 | 100 | 100 | 100 | 70 | 5 | 0 | 0 | 0 |
| 10. | 4 | PRE | 100 | 100 | 100 | 100 | 100 | 100 | 100 | 100 | 100 | 100 |
|  | 4 | POST | 100 | 100 | 100 | 100 | 100 | 35 | 25 | 60 | 60 | 70 |
| 11. | 4 | PRE | 0 | 100 | 100 | — | 85 | 25 | 100 | 15 | 0 | 0 |
|  | 4 | POST | 15 | 15 | 100 | 0 | 35 | 0 | 0 | 10 | 16 | 0 |
| 12. | 1 | PRE | 90 | 100 | 100 | 100 | 100 | 100 | 100 | 85 | 65 | 75 |
|  | 1 | POST | 100 | 100 | 100 | 100 | 100 | 100 | 60 | 55 | 20 | 100 |
| 13. | 1 | PRE | 80 | 100 | 100 | 100 | 100 | 100 | 100 | 25 | 60 | 80 |
|  | 1 | POST | 100 | 100 | 100 | 100 | 100 | 100 | 95 | 20 | 10 | 100 |
| 14. | 1 | PRE | 95 | 100 | 100 | 100 | 100 | 90 | 100 | 15 | 15 | 70 |

TABLE VI-continued

HERBICIDAL ACTIVITY

| Compound No. | Rate (lb/A) | Type | CKL | MG | PIG | SMT | VEL | BYG | FOX | JON | NUT | WO |
|---|---|---|---|---|---|---|---|---|---|---|---|---|
| | 1 | POST | 100 | 75 | 100 | 100 | 100 | 90 | 20 | 30 | 10 | 95 |
| 15. | 1 | PRE | 51 | 100 | 100 | 100 | 100 | 100 | 100 | 70 | 60 | 80 |
| | 1 | POST | 60 | 20 | 80 | 20 | 0 | 0 | 0 | 0 | 0 | 0 |
| 16. | 1 | PRE | 0 | 100 | 100 | 100 | 100 | 100 | 100 | 95 | 15 | 90 |
| | 1 | POST | 100 | 100 | 100 | 100 | 100 | 95 | 60 | 20 | 15 | 10 |
| 17. | 1 | PRE | 0 | 100 | 100 | 100 | 100 | 100 | 100 | 90 | 20 | 85 |
| | 1 | POST | 100 | 100 | 100 | 100 | 100 | 100 | 100 | 40 | 25 | 55 |
| 18. | 1 | PRE | 100 | 100 | 100 | 100 | 100 | 100 | 100 | 95 | 100 | 98 |
| | 1 | POST | 100 | 100 | 100 | 100 | 100 | 100 | 100 | 85 | 20 | 100 |
| 19. | 4 | PRE | — | 100 | 100 | 100 | 100 | 100 | 100 | 100 | 80 | 70 |
| | 4 | POST | 100 | 100 | 100 | 100 | 100 | 80 | 100 | 55 | 100 | 35 |
| 20. | 0.5 | PRE | — | 100 | 100 | 90 | 0 | 85 | 85 | 65 | 15 | 0 |
| | 0.5 | POST | 10 | 0 | 75 | 90 | 90 | 5 | 10 | 10 | 0 | 0 |
| 21. | 4 | PRE | 11 | 0 | 100 | 0 | 100 | 98 | 99 | 60 | 98 | 75 |
| | 4 | POST | 75 | 100 | 100 | 70 | 100 | 0 | 10 | 10 | 0 | 0 |
| 22. | 4 | PRE | 0 | 0 | 100 | 0 | 100 | 65 | 75 | 15 | 45 | 25 |
| | 4 | POST | 0 | 15 | 85 | — | 98 | 10 | 80 | 0 | 15 | 0 |
| 23. | 4 | PRE | 0 | 0 | 100 | 90 | 100 | 98 | 100 | 45 | 90 | 75 |
| | 4 | POST | — | 60 | 100 | 100 | 100 | 65 | 98 | 35 | 65 | 25 |
| 24. | 4 | PRE | 0 | 100 | 100 | 75 | 100 | 25 | 100 | 25 | 25 | 0 |
| | 4 | POST | 5 | 0 | 50 | 0 | 55 | 0 | 10 | 0 | 0 | 0 |
| 25. | 4 | PRE | 41 | 100 | 100 | 20 | 15 | 0 | 0 | 21 | 11 | 31 |
| | 4 | POST | 0 | 0 | 0 | 0 | 0 | 0 | 0 | 0 | 0 | 0 |
| 26. | 4 | PRE | 100 | 100 | 100 | 100 | 100 | 100 | 100 | 98 | 100 | 85 |
| | 4 | POST | 70 | 90 | 90 | 70 | 100 | 25 | 15 | 30 | 15 | 25 |
| 27. | 4 | PRE | — | 20 | 80 | 0 | 80 | 0 | 0 | 20 | 0 | 0 |
| | 4 | POST | 10 | 90 | 40 | 15 | 98 | 10 | 0 | 0 | 0 | 0 |
| 28. | 4 | PRE | 0 | 0 | — | 60 | 100 | 25 | 85 | 60 | 90 | 35 |
| | 4 | POST | 35 | 25 | 15 | 15 | 15 | 0 | 5 | 0 | 0 | 0 |
| 30. | 4 | PRE | 0 | 0 | 0 | 0 | 0 | 0 | 0 | 0 | 0 | 0 |
| | 4 | POST | 0 | 98 | 90 | 5 | 10 | 5 | 5 | 10 | 0 | 0 |
| 31. | 4 | PRE | 95 | 100 | 100 | 100 | 100 | 100 | 100 | 100 | 100 | 95 |
| | 4 | POST | 40 | 70 | 100 | 100 | 100 | 15 | 15 | 50 | 50 | 25 |
| 32. | 4 | PRE | 0 | 0 | — | 100 | 100 | 35 | 98 | 10 | 90 | 5 |
| | 4 | POST | 65 | 5 | 100 | 100 | 100 | 10 | 0 | 0 | 0 | 5 |
| 33. | 4 | PRE | 0 | 100 | — | 40 | 100 | 50 | 60 | 65 | 0 | 25 |
| | 4 | POST | 90 | 25 | 100 | 100 | 100 | 25 | 10 | 5 | 5 | 10 |
| 34. | 4 | PRE | — | 100 | — | 85 | 100 | 75 | 100 | 15 | 70 | 0 |
| | 4 | POST | 15 | 10 | 0 | 15 | 20 | 10 | 10 | 0 | 0 | 0 |
| 35. | 4 | PRE | 0 | 100 | — | 100 | 100 | 100 | 100 | 100 | 20 | 75 |
| | 4 | POST | 100 | 80 | 100 | 100 | 100 | 85 | 10 | 25 | 0 | 15 |
| 36. | 4 | PRE | 0 | 90 | — | 100 | 100 | 55 | 100 | 85 | 0 | 15 |
| | 4 | POST | 70 | 15 | 85 | 100 | 100 | 90 | 0 | 20 | 0 | 5 |
| 37. | 4 | PRE | 0 | 80 | — | 90 | 100 | 0 | 35 | 0 | 0 | 0 |
| | 4 | POST | 0 | 20 | 100 | — | 25 | 0 | 0 | 0 | 0 | 0 |
| 38. | 2 | PRE | 31 | 71 | 100 | 0 | 51 | 61 | 100 | 71 | 100 | 21 |
| | 2 | POST | 0 | 0 | 0 | 0 | 0 | 0 | 10 | 0 | 0 | 0 |
| 39. | 1 | PRE | 30 | 85 | 100 | 100 | 100 | 95 | 100 | 90 | 95 | 90 |
| | 1 | POST | 100 | 99 | 100 | 100 | 100 | 99 | 100 | 95 | — | 98 |
| 40. | 4 | PRE | — | 65 | — | — | 0 | 0 | 0 | 0 | 0 | 0 |
| | 4 | POST | 0 | 0 | — | 0 | — | 0 | 0 | 0 | 0 | 0 |
| 41. | 4 | PRE | 0 | 0 | 100 | 0 | 0 | 0 | 0 | 0 | 0 | 0 |
| | 4 | POST | 0 | 0 | 0 | 0 | 0 | 0 | 0 | 0 | 0 | 0 |
| 42. | 4 | PRE | 0 | 0 | 100 | 0 | 0 | 0 | 0 | 0 | 0 | 0 |
| | 4 | POST | 0 | 0 | 0 | 0 | 0 | 0 | 0 | 0 | 0 | 0 |
| 43. | 4 | PRE | — | 0 | 0 | 0 | 55 | 0 | 0 | — | 0 | 0 |
| | 4 | POST | — | 0 | 0 | 0 | 0 | 0 | 0 | 0 | 0 | 0 |
| 44. | 4 | PRE | 0 | 0 | 100 | 20 | 5 | 0 | 100 | 15 | 0 | 0 |
| | 4 | POST | 5 | 15 | 80 | 10 | 75 | 0 | 70 | 10 | 0 | 0 |
| 45. | 2 | PRE | 0 | 25 | 100 | 100 | 100 | 100 | 100 | 80 | 20 | 70 |
| | 2 | POST | 0 | 25 | 100 | 100 | 51 | 15 | 85 | 25 | 0 | 0 |
| 46. | 4 | PRE | — | 0 | 0 | 35 | 0 | 0 | 90 | 5 | 0 | 0 |
| | 4 | POST | — | 65 | 100 | 100 | 60 | 15 | 0 | 0 | 0 | 0 |
| 47. | 2 | PRE | 0 | 0 | 0 | 0 | 0 | 0 | 0 | 0 | 0 | 0 |
| | 2 | POST | 0 | 0 | 85 | 100 | 45 | 10 | 5 | 0 | 0 | 0 |
| 48. | 4 | PRE | 0 | 100 | 100 | 90 | 100 | 100 | 100 | 80 | 35 | 25 |
| | 4 | POST | 5 | 90 | 100 | 100 | 100 | 55 | 98 | 25 | 5 | 25 |
| 49. | 4 | PRE | 0 | 90 | 100 | 100 | 100 | 100 | 100 | 85 | 95 | 35 |
| | 4 | POST | 0 | 90 | 100 | 100 | 100 | 65 | 75 | 10 | 15 | 35 |
| 50. | 4 | PRE | 0 | 100 | 100 | 0 | 100 | 15 | 100 | 15 | 0 | 0 |
| | 4 | POST | 0 | 80 | 85 | 65 | 25 | 15 | 80 | 15 | 5 | 10 |
| 51. | 1 | PRE | 0 | 100 | 100 | 100 | 100 | 100 | — | 85 | 90 | 99 |
| | 1 | POST | 100 | 100 | 100 | 100 | 100 | 100 | 98 | 10 | 0 | 25 |
| 52. | 4 | PRE | 0 | 98 | 90 | 100 | 0 | 70 | 10 | 80 | 37 | 0 |
| | 4 | POST | 70 | 100 | 45 | 100 | 41 | 60 | 50 | 45 | 0 | 0 |
| 53. | 4 | PRE | 0 | 100 | 100 | 100 | 0 | 15 | 90 | 35 | 0 | 0 |
| | 4 | POST | 20 | 100 | 25 | 100 | 100 | 35 | 10 | 25 | 0 | 0 |
| 54. | 1 | PRE | 0 | 0 | 0 | — | 0 | 0 | 0 | 0 | 0 | 0 |
| | 1 | POST | 15 | 90 | 100 | 100 | 0 | 55 | 10 | 0 | 0 | 0 |
| 55. | 1 | PRE | 0 | 100 | 60 | 60 | 40 | 0 | 98 | 0 | 0 | 0 |

TABLE VI-continued

| | | HERBICIDAL ACTIVITY | | | | | | | | | |
|---|---|---|---|---|---|---|---|---|---|---|---|
| Compound No. | Rate (lb/A) | Type | CKL | MG | PIG | SMT | VEL | BYG | FOX | JON | NUT | WO |
| | 1 | POST | 100 | 100 | 95 | 100 | 70 | 55 | 98 | — | 0 | 0 |
| 56. | 1 | PRE | 0 | 100 | 100 | 0 | 0 | 0 | 90 | 0 | 0 | 0 |
| | 1 | POST | 100 | 100 | 100 | 100 | 90 | 80 | 90 | 0 | 0 | 0 |
| 57. | 1 | PRE | 0 | 100 | 100 | 100 | 100 | 0 | 0 | 0 | 0 | 0 |
| | 1 | POST | 35 | 85 | 100 | 95 | 100 | 5 | 10 | 0 | 0 | 0 |
| 58. | 1 | PRE | 0 | 65 | 100 | 0 | 100 | 10 | 80 | 10 | — | 0 |
| | 1 | POST | 100 | 100 | 100 | 100 | 100 | 65 | 100 | 21 | 20 | 15 |
| 59. | 1 | PRE | 0 | 0 | — | — | 0 | 15 | 70 | 0 | 0 | 0 |
| | 1 | POST | 55 | 30 | 75 | 100 | 100 | 10 | 60 | 5 | 5 | 5 |
| 60. | 1 | PRE | 0 | 0 | — | 60 | — | 10 | 0 | 15 | 0 | 0 |
| | 1 | POST | 10 | 15 | 15 | 45 | 100 | 5 | 0 | 5 | 0 | 0 |
| 61. | 1 | PRE | 10 | 100 | 100 | 100 | 100 | 100 | 100 | 98 | 15 | 80 |
| | 1 | POST | 30 | 30 | 75 | 100 | 90 | 65 | 95 | 15 | 0 | 10 |
| 62. | 1 | PRE | 0 | 100 | 100 | 100 | 0 | 0 | 0 | 0 | 0 | 0 |
| | 1 | POST | 5 | 85 | 0 | 70 | 0 | 15 | 55 | 0 | 0 | 0 |
| 63. | 4 | PRE | 0 | 100 | 100 | 99 | 95 | 65 | 60 | 25 | 0 | 0 |
| | 4 | POST | 0 | 35 | 35 | 45 | 100 | 0 | 0 | 0 | 0 | 0 |
| 64. | 1 | PRE | 35 | 100 | 100 | 100 | 100 | 40 | 100 | 85 | 100 | 75 |
| | 1 | POST | 20 | 20 | 15 | 90 | 85 | 0 | 0 | 0 | 0 | 0 |
| 65. | 4 | PRE | 0 | 0 | 0 | 0 | 0 | 0 | 0 | 0 | 0 | 0 |
| | 4 | POST | 0 | 60 | 40 | 0 | 70 | 5 | 0 | 0 | 0 | 0 |
| 66. | 1 | PRE | 20 | 100 | 100 | 75 | 100 | 100 | 100 | 85 | 85 | 35 |
| | 1 | POST | 45 | 95 | 100 | 100 | 100 | 20 | 85 | 20 | 25 | 0 |
| 67. | 1 | PRE | 0 | 70 | 100 | 100 | 100 | 100 | 100 | 90 | 60 | 70 |
| | 1 | POST | 30 | 70 | 35 | 95 | 100 | 0 | 20 | 0 | 65 | 0 |
| 68. | 1 | PRE | 0 | 90 | 100 | 100 | 95 | 55 | 100 | 65 | 15 | 10 |
| | 1 | POST | 30 | 25 | 80 | 100 | 100 | 10 | 55 | 10 | 10 | 10 |
| 69. | 4 | PRE | 10 | 100 | 100 | 100 | 100 | 100 | 100 | 100 | 95 | 80 |
| | 4 | POST | 15 | 90 | 100 | 100 | 100 | 10 | 90 | 15 | 0 | 0 |
| 70. | 1 | PRE | 0 | 100 | 100 | 100 | 100 | 25 | 100 | 100 | 0 | 65 |
| | 1 | POST | 55 | 80 | 40 | 100 | 100 | 0 | 100 | 15 | 10 | 0 |
| 71. | 1 | PRE | 0 | 100 | 100 | 100 | 100 | 0 | 100 | 20 | 0 | 0 |
| | 1 | POST | 25 | 40 | 65 | 100 | 30 | 0 | 10 | 0 | 0 | 0 |
| 72. | 4 | PRE | 50 | 85 | 100 | 100 | 100 | 100 | 100 | 100 | 70 | 100 |
| | 4 | POST | 60 | 98 | 100 | 75 | 100 | 35 | 100 | 30 | 15 | — |
| 73. | 4 | PRE | 10 | 100 | 100 | 100 | 100 | 100 | 100 | 100 | 10 | 15 |
| | 4 | POST | 0 | 60 | 95 | 100 | 100 | 75 | 100 | 60 | 15 | — |
| 74. | 4 | PRE | 0 | 0 | 100 | 85 | 0 | 0 | 0 | 10 | 0 | 0 |
| | 4 | POST | 20 | 60 | 45 | 35 | 60 | 0 | 0 | 0 | 0 | 0 |
| 75. | 4 | PRE | 0 | 75 | 100 | 100 | 98 | 0 | 50 | 10 | 0 | 0 |
| | 4 | POST | 35 | 60 | 25 | 100 | 80 | 0 | 20 | 15 | 10 | 25 |
| 76. | 4 | PRE | 0 | 95 | 100 | 100 | 100 | 98 | 100 | 100 | 0 | 15 |
| | 4 | POST | 25 | 75 | 50 | 100 | 100 | 90 | 60 | 100 | 0 | 80 |
| 79. | 1 | PRE | 100 | 100 | 100 | 100 | 100 | 100 | 100 | 100 | 98 | 100 |
| | 1 | POST | 100 | 100 | 100 | 100 | 100 | 100 | 100 | 100 | 100 | 80 |
| 80. | 4 | PRE | 0 | 0 | 99 | 0 | 35 | 0 | 0 | 0 | 0 | 0 |
| | 4 | POST | 0 | 0 | 0 | 0 | 0 | 0 | 0 | 0 | 10 | 0 |
| 81. | 4 | PRE | 15 | 10 | 100 | 100 | 100 | 80 | 85 | 90 | 80 | 70 |
| | 4 | POST | 98 | 0 | 100 | 0 | 95 | 30 | 35 | 15 | 10 | 0 |
| 82. | 1 | PRE | 0 | 100 | 100 | 100 | 100 | 100 | 100 | 100 | 100 | 100 |
| | 1 | POST | 100 | 100 | 100 | 100 | 100 | 100 | 100 | 100 | 100 | 90 |
| 83. | 1 | PRE | 80 | 100 | 100 | 100 | 100 | 100 | 100 | 100 | 100 | 85 |
| | 1 | POST | 100 | 100 | 100 | 100 | 100 | 100 | 100 | 100 | 100 | 80 |
| 84. | 1 | PRE | 0 | 55 | 100 | 100 | 30 | 0 | 0 | 0 | 0 | 0 |
| | 1 | POST | 0 | 0 | 95 | 0 | 0 | 0 | 0 | 60 | 0 | 0 |
| 85. | 4 | PRE | 0 | 0 | — | 20 | 45 | 0 | 0 | — | 0 | 0 |
| | 4 | POST | 0 | 0 | 0 | 0 | 0 | 0 | 0 | 0 | 0 | 0 |
| 86. | 4 | PRE | 0 | 100 | 100 | 100 | 100 | 100 | 100 | — | 20 | 99 |
| | 4 | POST | 10 | 30 | 55 | 65 | 100 | 90 | 100 | 70 | 45 | 40 |
| 87. | 1 | PRE | 20 | 100 | — | 100 | 100 | 85 | 100 | 100 | 100 | 100 |
| | 1 | POST | 100 | 20 | 100 | 98 | 100 | 40 | 100 | 80 | 35 | 0 |
| 88. | 1 | PRE | 0 | 0 | — | 80 | 15 | 0 | 0 | 0 | — | 0 |
| | 1 | POST | 0 | 0 | 0 | 0 | 0 | 0 | 0 | 0 | 0 | 0 |
| 89. | 1 | PRE | 100 | 100 | — | 100 | 100 | 100 | 100 | 100 | 0 | 80 |
| | 1 | POST | 20 | 65 | 100 | 95 | 95 | 15 | 95 | 20 | 98 | 0 |
| 90. | 1 | PRE | 15 | 100 | — | 100 | 100 | 85 | 100 | 100 | 30 | 25 |
| | 1 | POST | 60 | 100 | 100 | 100 | 100 | 0 | 65 | 70 | 99 | 0 |
| 91. | 1 | PRE | 20 | 50 | — | 100 | 65 | 100 | 100 | 100 | 10 | 0 |
| | 1 | POST | 0 | 30 | 40 | 70 | 10 | 0 | 65 | 35 | 35 | 0 |
| 92. | 1 | PRE | 0 | 0 | — | — | 15 | 40 | 100 | 15 | 0 | 0 |
| | 1 | POST | 10 | 15 | 10 | 100 | 45 | 0 | 25 | 0 | 0 | 0 |
| 93. | 4 | PRE | 55 | 100 | — | 100 | 100 | 100 | 100 | 100 | 60 | 100 |
| | 4 | POST | 45 | 100 | 100 | 95 | 100 | 100 | 98 | 100 | 98 | 100 |

TABLE VII

| | | | HERBICIDAL ACTIVITY | | | | | | | |
|---|---|---|---|---|---|---|---|---|---|---|
| Compound No. | Rate (lb./A) | Type | BID | NS | SMT | VEL | BYG | CRB | FOX | MF |
| 29. | 1 | PRE | 0 | 0 | 0 | 0 | 0 | 0 | 0 | 0 |
| | 1 | POST | 0 | 35 | 0 | 0 | 0 | 0 | 0 | 0 |
| 77. | 1 | PRE | 0 | 25 | 80 | 0 | 0 | 80 | 0 | 0 |
| | 1 | POST | 40 | — | 60 | 50 | 0 | 85 | 0 | 0 |
| 78. | 1 | PRE | 100 | 100 | 100 | 100 | 100 | 100 | 100 | 100 |
| | 1 | POST | 100 | — | 100 | 100 | 100 | 100 | 100 | 80 |
| 94. | 1 | PRE | — | 25 | 90 | 45 | 60 | — | 95 | — |
| | 1 | POST | — | 100 | 15 | 30 | 0 | — | 0 | — |
| 95. | 1 | PRE | — | 100 | 100 | 100 | 98 | — | 100 | — |
| | 1 | POST | — | 98 | 10 | 90 | 20 | — | 0 | — |
| 96. | 1 | PRE | 100 | 100 | 100 | 100 | 95 | 100 | 100 | 100 |
| | 1 | POST | 100 | 100 | 100 | 100 | 80 | 100 | 95 | 95 |
| 97. | 1 | PRE | 100 | 100 | 100 | 100 | 100 | 100 | 100 | 100 |
| | 1 | POST | 100 | 100 | 100 | 100 | 100 | 100 | 100 | 100 |
| 98. | 1 | PRE | 85 | 100 | 100 | 100 | 60 | 100 | 100 | 60 |
| | 1 | POST | 80 | 95 | 95 | 75 | 60 | 60 | 70 | 0 |
| 99. | 1 | PRE | 95 | 80 | — | 100 | 0 | — | 20 | — |
| | 1 | POST | 95 | 100 | 100 | 90 | 10 | 80 | 40 | 0 |
| 100. | 1 | PRE | 85 | 0 | 0 | 0 | 0 | 95 | 0 | 0 |
| | 1 | POST | 90 | — | 0 | 80 | 0 | 25 | 0 | 0 |
| 101. | 1 | PRE | 25 | 25 | 0 | 25 | 0 | 0 | 0 | 0 |
| | 1 | POST | 0 | 0 | 0 | 0 | 0 | 0 | 0 | 0 |
| 102. | 1 | PRE | 100 | 100 | 100 | 100 | 100 | 100 | 100 | 90 |
| | 1 | POST | 100 | 100 | 100 | 100 | 95 | 100 | 100 | 0 |
| 103. | 1 | PRE | 10 | 100 | 0 | 0 | 0 | 0 | 0 | 0 |
| | 1 | POST | 0 | 0 | 0 | 0 | 0 | 0 | 0 | 0 |
| 104. | 1 | PRE | 0 | 0 | 0 | 0 | 0 | 0 | 25 | 0 |
| | 1 | POST | 50 | 95 | 80 | 50 | 0 | 0 | 0 | 0 |
| 105. | 1 | PRE | 100 | 100 | 100 | 95 | 80 | 100 | 100 | 100 |
| | 1 | POST | 80 | 100 | 100 | 100 | 40 | 95 | 0 | 0 |
| 106. | 1 | PRE | 100 | 100 | 100 | 100 | 100 | 100 | 100 | 100 |
| | 1 | POST | 100 | 100 | 100 | 100 | 100 | 100 | 100 | 95 |
| 107. | 1 | PRE | 100 | 100 | 100 | 100 | 100 | 100 | 100 | 100 |
| | 1 | POST | 100 | 100 | 100 | 100 | 100 | 100 | 100 | 95 |
| 108. | 1 | PRE | 100 | 100 | 100 | 100 | 100 | 100 | 100 | 100 |
| | 1 | POST | 100 | 100 | 100 | 100 | 100 | 100 | 100 | 95 |
| 109. | 1 | PRE | 95 | 100 | 100 | 80 | 85 | 100 | 100 | 100 |
| | 1 | POST | 75 | 100 | 100 | 100 | 95 | 95 | 95 | 80 |
| 110. | 1 | PRE | 100 | 100 | 100 | 100 | 100 | 100 | 100 | 100 |
| | 1 | POST | 100 | 100 | 100 | 100 | 100 | 100 | 100 | 75 |
| 111. | 4 | PRE | 75 | 95 | 100 | 90 | 10 | 100 | 100 | 80 |
| | 4 | POST | 95 | 100 | 100 | 95 | 95 | 95 | 95 | 0 |
| 112. | 1 | PRE | 100 | 100 | 100 | 100 | 100 | 100 | 100 | 100 |
| | 1 | POST | 80 | 100 | 100 | 100 | 95 | 100 | 90 | 85 |
| 113. | 1 | PRE | 100 | 100 | 100 | 100 | 95 | 100 | 100 | 100 |
| | 1 | POST | 100 | — | 100 | 100 | 100 | 100 | 100 | 40 |
| 114. | 1 | PRE | 0 | — | 0 | 0 | 0 | 0 | 0 | 0 |
| | 1 | POST | 25 | 80 | 0 | 0 | 0 | 0 | 0 | 0 |
| 115. | 1 | PRE | 100 | 100 | 100 | 100 | 100 | 100 | 100 | 100 |
| | 1 | POST | 100 | — | 100 | 100 | 100 | 100 | 95 | 95 |
| 116. | 1 | PRE | 100 | — | 100 | 100 | 100 | 100 | 100 | 100 |
| | 1 | POST | 100 | 100 | 100 | 100 | 100 | 100 | 100 | 100 |
| 117. | 1 | PRE | 100 | — | 100 | 100 | 95 | 100 | 100 | 100 |
| | 1 | POST | 100 | 100 | 100 | 100 | 100 | 100 | 100 | 90 |
| 118. | 1 | PRE | 25 | — | — | 50 | 40 | 100 | 95 | 0 |
| | 1 | POST | 100 | 100 | 100 | 90 | 0 | 75 | 90 | 0 |
| 119. | 1 | PRE | 0 | 0 | 0 | 0 | 0 | 0 | 0 | 0 |
| | 1 | POST | 100 | 100 | 100 | 0 | 0 | 40 | 50 | 0 |
| 120. | 1 | PRE | 50 | 100 | 100 | 100 | 85 | 100 | 100 | 100 |
| | 1 | POST | 100 | 100 | 100 | 100 | 100 | 100 | 100 | 100 |
| 122. | 1 | PRE | 100 | 0 | 100 | 20 | 0 | 100 | 100 | 50 |
| | 1 | POST | 90 | 100 | 100 | 20 | 75 | 90 | 90 | 0 |
| 124 | 1 | PRE | 25 | 0 | 0 | 50 | 0 | 0 | 0 | 0 |
| | 1 | POST | 40 | 50 | 0 | 0 | 0 | 10 | 0 | 0 |
| 125. | 1 | PRE | 0 | 100 | 100 | 0 | 0 | 0 | 0 | 0 |
| | 1 | POST | 80 | 100 | 100 | 20 | 0 | 25 | 25 | 0 |
| 126. | 1 | PRE | 0 | 100 | 0 | 0 | 0 | 0 | 0 | 0 |
| | 1 | POST | 40 | 10 | 0 | 0 | 0 | 0 | 0 | 0 |
| 127. | 1 | PRE | 100 | 100 | 100 | 100 | 90 | 100 | 100 | 90 |
| | 1 | POST | 100 | 100 | 100 | 95 | 100 | 100 | 100 | 25 |
| 128. | 1 | PRE | 25 | 80 | 100 | 95 | 95 | 95 | 100 | 100 |
| | 1 | POST | 95 | 100 | 100 | 60 | 80 | 0 | 75 | 60 |
| 129. | 1 | PRE | 0 | 0 | 100 | 0 | 0 | 0 | 0 | 0 |
| | 1 | POST | 0 | 0 | 0 | 0 | 0 | 0 | 0 | 0 |
| 130. | 1 | PRE | 80 | 95 | 90 | 100 | 60 | 70 | 100 | 20 |
| | 1 | POST | 60 | 60 | 40 | 80 | 0 | 10 | 10 | 0 |
| 131. | 1 | PRE | 50 | 90 | 95 | 80 | 20 | 60 | 95 | 40 |
| | 1 | POST | 10 | 100 | 100 | 25 | 0 | 0 | 60 | 0 |
| 132. | 1 | PRE | 95 | 95 | 100 | 100 | 95 | 100 | 100 | 100 |
| | 1 | POST | 95 | 100 | 100 | 100 | 95 | 10 | 100 | 95 |

TABLE VII-continued

| Compound No. | Rate (lb./A) | Type | HERBICIDAL ACTIVITY BID | NS | SMT | VEL | BYG | CRB | FOX | MF |
|---|---|---|---|---|---|---|---|---|---|---|
| 133. | 1 | PRE | 90 | 100 | 100 | 100 | 90 | 100 | 100 | 100 |
|  | 1 | POST | 100 | 100 | 100 | 100 | 70 | 25 | 100 | 95 |
| 134. | 1 | PRE | 0 | 0 | 100 | 95 | 0 | 0 | 40 | 0 |
|  | 1 | POST | 100 | 100 | 100 | 80 | 10 | 0 | 20 | 0 |
| 135. | 1 | PRE | 25 | 40 | 50 | 80 | 0 | 90 | 95 | 80 |
|  | 1 | POST | 95 | 100 | 10 | 75 | 0 | 10 | 20 | 0 |
| 137. | 1 | PRE | 100 | 100 | 100 | 100 | 100 | 100 | 100 | 100 |
|  | 1 | POST | 60 | 100 | 100 | 95 | 25 | 10 | 80 | 50 |
| 138. | 1 | PRE | 100 | 100 | 100 | 100 | 100 | 100 | 100 | 100 |
|  | 1 | POST | 100 | 100 | 100 | 100 | 95 | 90 | 100 | 100 |
| 140. | 1 | PRE | 0 | 75 | 0 | 0 | 0 | 0 | 0 | 0 |
|  | 1 | POST | 60 | 95 | 75 | 40 | 0 | 0 | 0 | 0 |
| 142. | 1 | PRE | 0 | 0 | 0 | 0 | 0 | 0 | 0 | 0 |
|  | 1 | POST | 10 | 10 | 25 | 0 | 0 | 20 | 10 | 0 |
| 143. | 1 | PRE | 0 | 0 | 0 | 0 | 0 | 0 | 0 | 0 |
|  | 1 | POST | 30 | 25 | 0 | 0 | 0 | 0 | 20 | 0 |
| 144. | 1 | PRE | 100 | 0 | 0 | 0 | 0 | 0 | 0 | 0 |
|  | 1 | POST | 0 | 50 | 0 | 0 | 0 | 0 | 0 | 0 |
| 145. | 1 | PRE | 100 | 100 | 100 | 100 | 95 | 100 | 95 | 100 |
|  | 1 | POST | 100 | 100 | 100 | 100 | 100 | 95 | 95 | 95 |
| 146. | 1 | PRE | 0 | 0 | 0 | 0 | 0 | 0 | 0 | 0 |
|  | 1 | POST | 20 | 0 | 0 | 0 | 0 | 0 | 0 | 0 |
| 147. | 1 | PRE | 100 | 100 | 100 | 100 | 100 | 100 | 100 | 100 |
|  | 1 | POST | 100 | 100 | 100 | 100 | 100 | 100 | 100 | 100 |
| 148. | 1 | PRE | 90 | 90 | 60 | 85 | 0 | 25 | 60 | 0 |
|  | 1 | POST | 95 | 90 | 80 | 95 | 0 | 0 | 0 | 0 |
| 149. | 1 | PRE | 100 | 100 | 100 | 100 | 95 | 100 | 100 | 100 |
|  | 1 | POST | 100 | 100 | 100 | 100 | 100 | 100 | 100 | 85 |
| 150. | 1 | PRE | 0 | 70 | 0 | 25 | 10 | 100 | 95 | 40 |
|  | 1 | POST | 0 | 0 | 0 | 0 | 0 | 0 | 0 | 0 |
| 151. | 1 | PRE | 0 | 100 | 100 | 100 | 25 | 90 | 80 | 90 |
|  | 1 | POST | 70 | 100 | 100 | 85 | 10 | 20 | 20 | 10 |
| 152. | 1 | PRE | 40 | 100 | 100 | 25 | 60 | 100 | 100 | 75 |
|  | 1 | POST | 30 | 100 | 95 | 25 | 0 | 0 | 20 | 0 |
| 153. | 1 | PRE | 20 | 100 | 95 | 90 | 0 | 60 | 0 | 0 |
|  | 1 | POST | 40 | 100 | 100 | 95 | 0 | 0 | 0 | 0 |
| 154. | 1 | PRE | 75 | — | — | 100 | 0 | 100 | 60 | 85 |
|  | 1 | POST | 95 | 100 | 100 | 100 | 70 | 10 | 70 | 0 |
| 155. | 1 | PRE | 100 | 100 | 100 | 100 | 80 | 100 | 100 | 90 |
|  | 1 | POST | 100 | 100 | 100 | 100 | 50 | 90 | 80 | 0 |
| 156. | 1 | PRE | 90 | 100 | 100 | 100 | 90 | 100 | 100 | 100 |
|  | 1 | POST | 100 | 100 | 100 | 100 | 95 | 100 | 100 | 95 |
| 157. | 1 | PRE | 100 | 100 | 100 | 100 | 95 | 100 | 100 | 100 |
|  | 1 | POST | 100 | 100 | 100 | 100 | 100 | 100 | 100 | 60 |
| 158. | 1 | POST | 95 | 100 | 95 | 100 | 20 | 10 | 20 | 0 |
| 159. | 1 | PRE | 100 | 100 | 100 | 100 | 100 | 100 | 100 | 100 |
|  | 1 | POST | 60 | 100 | 100 | 80 | 100 | 100 | 100 | 90 |
| 160. | 1 | PRE | 70 | 100 | 95 | 85 | 20 | 95 | 20 | 40 |
|  | 1 | POST | 100 | 100 | 0 | 100 | 20 | 80 | 30 | 0 |
| 161. | 1 | PRE | 0 | 50 | 0 | 0 | 0 | 0 | 0 | 0 |
|  | 1 | POST | 25 | 100 | 25 | 60 | 0 | 10 | 10 | 0 |
| 162 | 1 | PRE | 0 | 25 | 100 | 0 | 0 | 80 | 40 | 0 |
|  | 1 | POST | 95 | 100 | 100 | 90 | 35 | 25 | 85 | 0 |
| 163. | 1 | PRE | 0 | 0 | 0 | 0 | 0 | 0 | 0 | 0 |
|  | 1 | POST | 30 | 20 | 0 | 0 | 0 | 0 | 0 | 0 |

The glutaramic acid compounds of the instant invention are also useful as algicides. The compounds may be advantageously used to either prevent or control the growth of algae. The exact amount of glutaramic acid required will, of course, vary with the medium being protected, the algae being controlled, the particular glutaramic acid being employed and other factors known to one skilled in the art.

The glutaramic acids of the present invention, when used for the control of algae, can be used in any of the types of formulations disclosed above for the control of undesired plants. These formulations include liquid solutions, such as emulsifiable concentrates and dilute sprays, and dry powders such as wettable powders and dusts.

The algicidal and algistatic activities of the compounds of the instant invention were determined by the following procedure.

In separate wells of a microtiter plate (Plate A) were placed 100 μserial dilutions of the compound to be tested in modified Allen's medium, described below. In addition, one well contained only modified Allen's medium (no compound) as a control. Each well of the plate was then inoculated with a mixed algae culture. The plates were covered with clear plastic lids and placed in a clear plastic bag along with several moistened paper towels to create high humidity and prevent evaporation from the plates.

The plastic bags containing the plates were placed in high light conditions (200-700 foot candles) at room temperature. After 14 days the minimal inhibitory concentration (MIC) needed to inhibit growth was determined from Plate A. The effect of inhibiting growth is defined as the static effect. To read the microtiter plates for static or cidal activity, a stereoscope were used at low magnification to observe growth or no growth in each well. Plate readers were also used to read growth or no growth.

The following procedure was used to prepare modified Allen's medium.

Seven stock solutions were prepared as follows:

| | |
|---|---|
| NaNO₃ | 10.0 g in 400 ml deionized water |
| CaCl₂ | 1.0 g in 400 ml deionized water |
| MgSO₄.7H₂O | 3.0 g in 400 ml deionized water |
| K₂HPO₄ | 3.0 g in 400 ml deionized water |
| KH₂PO₄ | 7.0 g in 400 ml deionized water |
| NaCl | 1.0 g in 400 ml deionized water |
| FeCl₃ | 1.0 g in 100 ml deionized water |

Each of the above stock solutions was filter sterilized.

To 940 ml of sterile deionized water, was added 1 drop of the FeCl₃ solution and 10.0 ml of all the other stock solutions. The ambient pH of this medium was about 6.1 and the water hardness was about 65 ppm, expressed as calcium carbonate. The pH and hardness was adjusted to the pH value of Table VIII with sterile 1 normal (N) KOH or HCl for pH and the water hardness of Table VIII with a sterile NaHCO₃ solution (56.03 g NaHCO₃ in 1.0 liter of boiled and distilled water, then filtered and sterilized.

The mixed algae culture was obtained from an industrial cooling tower in Spring House, Pa. and maintained in the laboratory by means commonly known. The mixed culture contained green algae and blue-green bacteria.

The algicidal activity (in ppm) of compounds of the present invention in modified Allen's medium under 750 foot candles of light is shown in Table VIII.

TABLE VIII

| Algicidal Activity | |
|---|---|
| Compound No. | pH 8 200 ppm static |
| 1 | 250 |
| 10 | 250 |
| 13 | <2 |
| 16 | 250 |
| 20 | 125 |
| 21 | >250 |
| 23 | >250 |
| 26 | 250 |
| 30 | <2 |
| 31 | >250 |
| 35 | 125 |
| 37 | 250 |
| 47 | >250 |
| 49 | 16 |
| 51 | 250 |
| 52 | 250 |
| 53 | 250 |
| 54 | 250 |
| 60 | 250 |
| 64 | 125 |
| 66 | 250 |
| 68 | 250 |
| 70 | >250 |
| 71 | 250 |

It is to be understood that changes and variations may be made without departing from the spirit and scope of the invention as defined by the appended claims.

What is claimed is:

1. A compound of the formula $$\underset{Y\ \ D\ \ X}{\overset{T}{Z\!-\!\!\bigcirc\!\!-\!(O)_n\!-\!\overset{H}{N}\!-\!\overset{O}{\overset{\|}{C}}\!-\!CH_2\!-\!\overset{R}{\underset{R^2}{C}}\!-\!\overset{R^1}{\underset{}{CH}}\!-\!A}} \quad I$$

wherein

A is hydroxymethyl, chloromethyl, carboxy, carboxy salt, alkoxycarbonyl or alkylaminocarbonyl;

D is nitrogen;

n is 0 or 1;

R is hydrogen, $(C_1-C_4)$alkyl, halo$(C_1-C_4)$alkyl containing from one to nine halo atoms, or phenyl;

$R^1$ is hydrogen, $(C_1-C_2)$alkyl or halo$(C_1-C_2)$alkyl;

$R^2$ is hydrogen or $(C_1-C_2)$alkyl;

T is hydrogen or fluorine;

X is hydrogen or halogen;

Y is hydrogen, halo$(C_1-C_3)$alkyl, $(C_1-C_3)$alkyl, cyano, nitro, halogen, phenoxy or phenylthio, provided when Y is hydrogen, R is trifluoromethyl, and $R^1$ and $R^2$ are hydrogen and Z is not hydrogen; and when Y is chlorine and Z is a substituent linked to the phenyl ring by oxygen, R is not hydrogen; and Z is hydrogen, hydroxy, halogen, alkoxy, alkenyloxy, alkynyloxy, alkylthio, alkenylthio, alkynylthio, carboxyalkoxy, carboxyalkylthio, alkoxycarbonylalkoxy, alkoxycarbonylalkylthio, cycloalkoxy, cycloalkylalkoxy, cycloalkylthio, cycloalkylalkylthio, formyl, alkanoyl, alkoxycarbonyl, alkenyloxycarbonyl, alkynyloxycarbonyl, cycloalkoxycarbonyl, cycloalkylalkoxycarbonyl, alkoxycarbonylalkoxycarbonyl, alkyl, hydroxyalkyl, alkoxyalkyl, alkenyloxyalkyl, alkynyloxyalkyl, alkylthioalkyl, alkenylthioalkyl, alkynylthioalkyl, cycloalkoxyalkyl, cycloalkylalkoxyalkyl, cycloalkylthioalkyl, cycloalkylalkylthioalkyl, alkoxycarbonylalkoxyalkyl, phenoxyalkyl, phenylthioalkyl, alkylaminoalkyl, oximyl, alkyloximyl, alkenyloximyl, alkynyloximyl, alkoxycarbonylalkyloximyl, alkyl(alkyl)oximyl, alkenyl(alkyl)oximyl, alkynyl(alkyl)oximyl, alkoxycarbonylalkyl(alkyl)oximyl, alkylamino, monoalkenylamino, monoalkynylamino, or alkanoylamino.

2. A compound of claim 1 wherein

A is CH₂OH, CH₂Cl, COOH, COO—M+ wherein M+ is an agronomically acceptable salt, $(C_1-C_6)$alkoxycarbonyl, or $(C_1-C_6)$alkylaminocarbonyl;

n is 0;

D is nitrogen;

R is hydrogen, $(C_1-C_4)$alkyl, halo$(C_1-C_4)$alkyl or phenyl;

$R^1$ is hydrogen or $(C_1-C_2)$alkyl;

$R^2$ is hydrogen or $(C_1-C_2)$alkyl;

T is hydrogen or fluorine;

X is hydrogen or halogen, provided that when X and Z are each independently hydrogen or halogen, Y is halogen and R must be trifluoromethyl;

Y is hydrogen, halogen, trifluoromethyl, phenoxy, cyano or nitro, provided when Y is hydrogen, R is trifluoromethyl and $R^1$ and $R^2$ are hydrogen and Z is not hydrogen; and when Y is chlorine and Z is a substituent linked to the phenyl ring by oxygen, R is not hydrogen; and Z is hydrogen, halogen, $(C_1-C_6)$alkoxy, $(C_3-C_6)$alkenyloxy, $(C_3-C_6)$alkynyloxy, $(C_1-C_6)$alkylthio, (C$_3$-C$_6$)alkenylthio, (C$_3$-C$_6$)alkynylthio, phenyl(C$_1$-C$_6$)alkoxy, phenyl(C$_1$-C$_6$)alkylthio, carboxy(C$_1$-C$_6$)alkythio, (C$_1$-C$_6$)alkoxycarbonyl(C$_1$-C$_6$)alkylthio, (C$_1$-C$_6$)alkanoyl, (C$_1$-C$_6$)alkoxycarbonyl, (C$_3$-C$_6$)cycloalkoxycarbonyl, (C$_1$-C$_6$)(C$_1$-C$_6$)alkanoyl, (C$_1$-C$_6$)alkoxycarbonyl, (C$_3$-C$_6$)cycloalkoxycarbonyl, (C$_3$-C$_6$)cycloalkyl (C$_1$-C$_6$)alkoxycarbonyl, (C$_1$-C$_6$)alkoxycarbonyl(C$_1$-C$_6$)alkoxycarbonyl, (C$_1$-C$_6$)alkyl, hydroxy(C$_1$-C$_6$)alkyl, (C$_1$-C$_6$)alkoxy(C$_1$-C$_6$)alkyl, (C$_3$-C$_6$)alkenyloxy(C$_1$-C$_6$)alkyl, (C$_3$-C$_6$)alkynyloxy(C$_1$-C$_6$)alkyl, (C$_1$-C$_6$)alkythio(C$_1$-C$_6$)alkyl, (C$_1$-C$_6$)alkoxycarbonyl(C$_1$-C$_6$)alkoxy(C$_1$-C$_6$)alkyl, phenoxy(C$_1$-C$_6$)alkyl, phenylthio(C$_1$-C$_6$)alkyl, or di(C$_1$-C$_6$)alkylamino(C$_1$-C$_6$)alkyl.

3. The compound of claim 2 wherein
A is CO$_2$H, (C$_1$-C$_6$)alkoxycarbonyl or CO$_2$—M+;
n is 0;
R is (C$_1$-C$_4$)alkyl or halo(C$_1$-C$_4$)alkyl;
R$^1$ is hydrogen or (C$_1$-C$_2$)alkyl;
R$^2$ is hydrogen;
X is hydrogen or halogen;
Y is hydrogen or halogen;
T is hydrogen or fluorine;
Z is hydrogen, (C$_1$-C$_6$)alkoxy, (C$_3$-C$_6$)alkenyloxy, (C$_3$-C$_6$)alkynyloxy, (C$_1$-C$_6$)alkylthio, (C$_3$-C$_6$)alkenylthio, (C$_3$-C$_6$)alkynylthio, phenyl(C$_1$-C$_6$)alkoxy, phenyl(C$_1$-C$_6$)alkylthio, carboxy(C$_1$-C$_6$)alkylthio, or (C$_1$-C$_6$)alkoxycarbonyl(C$_1$-C$_6$)alkylthio.

4. The compound of claim 3 wherein A is carboxy, (C$_1$-C$_6$)alkoxycarbonyl or CO$_2$—M+; n is 0; R is CH$_3$, CF$_3$ or CF$_2$CF$_3$; R$^1$ is H; X is Cl or F; Y is Br, F, or Cl; T is H; and Z is (C$_1$-C$_6$)alkoxy, (C$_3$-C$_6$)alkenyloxy, or (C$_3$-C$_6$)alkynyloxy.

5. The compound of claim 4 wherein A is carboxy, ethoxycarbonyl, methoxycarbonyl, isopropyloxycarbonyl, isopropylammonium carboxylate or potassium carboxylate; X is F; Y is Cl; and Z is propargyloxy, allyloxy, n-propyloxy, isopropyloxy, ethoxy or methoxy.

6. The compound of claim 5 wherein A is COOH; R is CF$_3$; and Z is propargyloxy, isopropyloxy, n-propyloxy, ethoxy, methoxy or allyloxy.

7. The compound of claim 5 wherein R is CH$_3$; A is COOH; and Z is propargyloxy.

8. The compound of claim 5 wherein R is CF$_2$CF$_3$; A is COOH; and Z is propargyloxy.

9. The compound of claim 5 wherein R is CF$_3$; Z is propargyloxy; and A is carboxy, ethoxycarbonyl, methoxycarbonyl, isopropyloxycarbonyl, isopropylammonium carboxylate or potassium carboxylate.

10. The compound of claim 5 wherein R is CF$_3$; Z is isopropyloxy; and A is carboxy or methoxycarbonyl.

11. The compound of claim 2 wherein
A is carboxy;
n is 0;
R is (C$_1$-C$_4$)alkyl or halo(C$_1$-C$_4$)alkyl;
R$^1$ is H or (C$_1$-C$_2$)alkyl;
R$^2$ is H;
X is H or halogen;
Y is H or halogen;
T is H or F; and
Z is (C$_1$-C$_6$)alkoxycarbonyl;
or its agronomically acceptable salts.

12. The compound of claim 11 wherein A is COOH; R is CF$_3$; R$^1$ is hydrogen; X is Cl or F; Y is Br, F or Cl; T is hydrogen; and Z is (C$_1$-C$_6$)alkoxycarbonyl.

13. The compound of claim 12 wherein X is F; Y is Cl; and Z is isopropyloxycarbonyl.

14. The compound of claim 2 wherein
A is carboxy;
n is 0;
R is (C$_1$-C$_4$)alkyl or halo(C$_1$-C$_4$)alkyl;
R$^1$ is H or (C$_1$-C$_2$)alkyl;
R$^2$ is H;
X is H or halogen;
Y is H or halogen;
T is H or F; and
Z is (C$_1$-C$_6$)alkoxy(C$_1$-C$_6$)alkyl, (C$_3$-C$_6$)alkenyloxy(C$_1$-C$_6$)alkyl or (C$_3$-C$_6$)alkynyloxy(C$_1$-C$_6$)alkyl;
or its agronomically acceptable salts.

15. The compound of claim 14 wherein A is carboxy; n is 0; R is CF$_3$; R$^1$ is hydrogen; X is Cl or F; Y is Br, F or Cl; T is hydrogen; and Z is (C$_1$-C$_6$)alkoxy(C$_1$-C$_6$)alkyl, (C$_3$-C$_6$)alkenyloxy(C$_1$-C$_6$)alkyl or (C$_3$-C$_6$)alkynyloxy(C$_1$-C$_6$)alkyl.

16. The compound of claim 15 wherein X is F, Y is Cl, and Z is isopropyloxymethyl or 1-methylpropargyloxymethyl.

17. A herbicidal composition comprising an agronomically acceptable carrier and a herbicidally effective amount of the compound of claim 5.

18. A herbicidal composition comprising an agronomically acceptable carrier and a herbicidally effective amount of the compound of claim 6.

19. A herbicidal composition comprising an agronomically acceptable carrier and a herbicidally effective amount of the compound of claim 7.

20. A herbicidal composition comprising an agronomically acceptable carrier and a herbicidally effective amount of the compound of claim 8.

21. A herbicidal composition comprising an agronomically acceptable carrier and a herbicidally effective amount of the compound of claim 9.

22. A herbicidal composition comprising an agronomically acceptable carrier and a herbicidally effective amount of the compound of claim 10.

23. A herbicidal composition comprising an agronomically acceptable carrier and a herbicidally effective amount of the compound of claim 11.

24. A herbicidal composition comprising an agronomically acceptable carrier and a herbicidally effective amount of the compound of claim 12.

25. A herbicidal composition comprising an agronomically acceptable carrier and a herbicidally effective amount of the compound of claim 13.

26. A herbicidal composition comprising an agronomically acceptable carrier and a herbicidally effective amount of the compound of claim 14.

27. A herbicidal composition comprising an agronomically acceptable carrier and a herbicidally effective amount of the compound of claim 15.

28. A herbicidal composition comprising an agronomically acceptable carrier and a herbicidally effective amount of the compound of claim 16.

29. A method for controlling unwanted plants which comprises applying to the plant or growth medium therefore the compound of claim 9.

30. A method for controlling unwanted plants which comprises applying to the plant or growth medium therefore the compound of claim 10.

31. A method for controlling unwanted plants which comprises applying to the plant or growth medium therefore the compound of claim 11.

32. A method for controlling unwanted plants which comprises applying to the plant or growth medium therefore the compound of claim 12.

33. A method for controlling unwanted plants which comprises applying to the plant or growth medium therefore the compound of claim 13.

34. A method for controlling unwanted plants which comprises applying to the plant or growth medium therefore the compound of claim 14.

35. A method for controlling unwanted plants which comprises applying to the plant or growth medium therefore the compound of claim 15.

36. A method for controlling unwanted plants which comprises applying to the plant or growth medium therefore the compound of claim 16.

37. The method of claim 29 wherein the compound is applied at a rate of from about 0.001 to about 12 pounds per acre.

38. The method of claim 37 wherein the compound is applied at a rate of from about 0.01 to about 5 pounds per acre.

* * * * *